US012735375B2

(12) United States Patent
Bailey et al.

(10) Patent No.: US 12,735,375 B2
(45) Date of Patent: Sep. 15, 2026

(54) PROCESS FOR HYDROGENATION OF A GLYCEROL ESTER

(71) Applicant: JOHNSON MATTHEY PUBLIC LIMITED COMPANY, London (GB)

(72) Inventors: Rowan Bailey, Cambridge (GB); Damian Grainger, Cambridge (GB); Antonio Zanotti-Gerosa, Cambridge (GB)

(73) Assignee: Johnson Matthey Public Limited Company, London (GB)

( * ) Notice: Subject to any disclaimer, the term of this patent is extended or adjusted under 35 U.S.C. 154(b) by 717 days.

(21) Appl. No.: 18/043,699

(22) PCT Filed: Nov. 3, 2021

(86) PCT No.: PCT/GB2021/052849

§ 371 (c)(1),
(2) Date: Mar. 1, 2023

(87) PCT Pub. No.: WO2022/096874

PCT Pub. Date: May 12, 2022

(65) Prior Publication Data

US 2023/0373890 A1 Nov. 23, 2023

(30) Foreign Application Priority Data

Nov. 4, 2020 (GB) ..................................... 2017457

(51) Int. Cl.
*C07C 29/149* (2006.01)
*C07F 15/00* (2006.01)

(52) U.S. Cl.
CPC ........ *C07C 29/149* (2013.01); *C07F 15/0053* (2013.01)

(58) Field of Classification Search
CPC .................................................... C07C 29/149
See application file for complete search history.

(56) References Cited

U.S. PATENT DOCUMENTS

| | | | | |
|---|---|---|---|---|
| 8,344,187 | B2 | 1/2013 | Ikariya et al. | |
| 2014/0328748 | A1* | 11/2014 | Goussev | C07F 15/0046 568/864 |

FOREIGN PATENT DOCUMENTS

| | | | |
|---|---|---|---|
| CN | 109956970 | A | 7/2019 |
| CN | 110105399 | A | 8/2019 |
| JP | 2010-37329 | A | 2/2010 |
| JP | 2013-6774 | A | 1/2013 |
| WO | 2013/023307 | A1 | 2/2013 |
| WO | 2019/175158 | A1 | 9/2019 |

OTHER PUBLICATIONS

Machine translation of CN109956970A, Dec. 26, 2017, pp. 1-37 (Year: 2017).*

Spasyuk, D. et al. "Replacing Phosphorus with Sulfur for the Efficient Hydrogenation of Esters" Angew. Chem. Int. Ed. 2013, 52, 2538 -2542, https://doi.org/10.1002/anie.201209218Digital (Year: 2013).*

* cited by examiner

*Primary Examiner* — Medhanit W Bahta
(74) *Attorney, Agent, or Firm* — BakerHostetler

(57) ABSTRACT

The present invention relates to a process for hydrogenation of a glycerol ester, comprising treating a composition which comprises a glycerol ester with a base and a transition metal catalyst in the presence of molecular hydrogen, wherein the base is present in at least 7 wt % based upon the total weight of said composition and wherein the catalyst is present in less than or equal to 0.05 wt % based upon the total weight of said composition.

24 Claims, 2 Drawing Sheets

PROCESS FOR HYDROGENATION OF A GLYCEROL ESTER

FIELD OF THE INVENTION

The present invention is directed to a process for the hydrogenation of glycerol esters.

BACKGROUND TO THE INVENTION

The reduction of esters is an essential transformation in the chemical industry as a route to primary alcohols. The reduction of esters has conventionally been carried out using reagents (in stoichiometric or excess quantities) such as sodium metal in ethanol (the Bouveault-Blanc reduction) or more recently with a metal hydride reagent, such as $LiAlH_4$ or $NaBH_4$. These reduction reactions are, however, difficult to carry out effectively on a large scale, not least due to safety concerns associated with an extremely exothermic quenching step. As such, large scale catalytic reduction reactions use hydrogen gas. Cu- or Zn-based heterogeneous catalysts are used for ester reduction, primarily in the Natural Detergent Alcohol (NDA) market on very large scale. However, these methods require very high pressures and/or temperatures, in large scale, dedicated production facilities. The chemoselectivity for ester reduction compared to other sensitive functional groups can also be problematic in some cases using these methods. Furthermore, the industrial processes for the conversion of glycerol esters to primary alcohols using Cu- or Zn-based heterogeneous catalysts currently include an intermediate step in which the glycerol ester is hydrolysed to yield a fatty acid(s) which are then transesterified with a lower alcohol to form a fatty acid ester(s). Alternatively, glycerol esters are directly transesterified with a lower alcohol to form a fatty acid ester(s). The direct reduction of glycerol esters is not utilised industrially due to the reduction of glycerol to propylene glycol which requires more hydrogen, a higher catalyst cost and destroys the valuable glycerol by-product.

Accordingly, there exists a need to provide an improved process for hydrogenation of glycerol esters that requires a lower catalyst loading whilst still maintaining high catalyst activity and TON.

SUMMARY OF THE INVENTION

The present invention provides an improved process for the hydrogenation of glycerol esters. The process is simple, economical, safe and can be operated in standard hydrogenation vessels. In certain embodiments, the process may have environmental benefits by requiring the use of much lower amounts of catalyst than is used in conventional processes.

In a first aspect, the present invention provides a process for hydrogenation of a glycerol ester, comprising treating a composition which comprises a glycerol ester with a base and a transition metal catalyst in the presence of molecular hydrogen, wherein the base is present in at least 7 wt % based upon the total weight of said composition and wherein the catalyst is present in less than or equal to 0.05 wt % based upon the total weight of said composition.

In a further aspect, the present invention provides a hydrogenated composition obtained by or obtainable by the process as hereinbefore described.

In a further aspect, the present invention provides a method of making a compound, comprising a process as hereinbefore described.

Definitions

The point of attachment of a moiety or substituent is represented by "—". For example, —OH is attached through the oxygen atom.

As used herein, the term "alkyl" refers to a straight-chain or branched saturated hydrocarbon group. In certain embodiments, the alkyl group may have from 1-20 carbon atoms, in certain embodiments from 1-15 carbon atoms, in certain embodiments, 1-8 carbon atoms. The alkyl group may be unsubstituted. Alternatively, the alkyl group may be substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, n-butyl, iso-butyl, sec-butyl, tert-butyl, n-pentyl, n-hexyl and the like.

As used herein, the term "alkenyl" refers to a straight-chain or branched unsaturated hydrocarbon group comprising at least one carbon-carbon double bond.

As used herein, the term "alkynyl" refers to a straight-chain or branched unsaturated hydrocarbon group comprising at least one carbon-carbon triple bond.

As used herein, the term "cycloalkyl" is used to denote a saturated carbocyclic hydrocarbon radical. The cycloalkyl group may have a single ring or multiple condensed rings. In certain embodiments, the cycloalkyl group may have from 3-15 carbon atoms, in certain embodiments, from 3-10 carbon atoms, in certain embodiments, from 3-8 carbon atoms. The cycloalkyl group may be unsubstituted. Alternatively, the cycloalkyl group may be substituted. Unless other specified, the cycloalkyl group may be attached at any suitable carbon atom and, if substituted, may be substituted at any suitable atom. Typical cycloalkyl groups include but are not limited to cyclopropyl, cyclobutyl, cyclopentyl, cyclohexyl, adamantyl and the like.

As used herein, the term "cycloalkenyl" refers to an unsaturated, non-aromatic carbocyclic ring. The cycloalkenyl group therefore has at least one carbon-carbon double bond, but may have more. In certain embodiments, the cycloalkenyl group may have from 3-15 carbon atoms, in certain embodiments, from 3-10 carbon atoms, in certain embodiments, from 3-8 carbon atoms. The cycloalkenyl group may be unsubstituted. Alternatively, the cycloalkenyl group may be substituted. Unless other specified, the cycloalkenyl group may be attached at any suitable carbon atom and, if substituted, may be substituted at any suitable atom. Typical cycloalkenyl groups include but are not limited to cyclopropenyl, cyclobutenyl, cyclopentenyl, cyclohexenyl, and the like.

As used herein, the term "alkoxy" refers to an optionally substituted group of the formula alkyl-O— or cycloalkyl-O—, wherein alkyl and cycloalkyl are as defined above.

As used herein, the term "aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-12 carbon atoms. The aryl group may be unsubstituted. Alternatively, the aryl group may be substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

As used herein, the term "arylalkyl" refers to an optionally substituted group of the formula aryl-alkyl-, where aryl and alkyl are as defined above.

As used herein, the term "halogen", "halo" or "hal" refers to —F, —Cl, —Br and —I.

As used herein, the term "heteroalkyl" refers to a straight-chain or branched saturated hydrocarbon group wherein one or more carbon atoms are independently replaced with one or more heteroatoms (e.g. nitrogen, oxygen, phosphorus and/or sulfur atoms). The heteroalkyl group may be unsubstituted. Alternatively, the heteroalkyl group may be substituted. Unless otherwise specified, the heteroalkyl group may be attached at any suitable atom and, if substituted, may be substituted at any suitable atom. Examples of heteroalkyl groups include but are not limited to ethers, thioethers, primary amines, secondary amines, tertiary amines and the like.

As used herein, the term "heterocycloalkyl" refers to a saturated cyclic hydrocarbon group wherein one or more carbon atoms are independently replaced with one or more heteroatoms (e.g. nitrogen, oxygen, phosphorus and/or sulfur atoms). The heterocycloalkyl group may be unsubstituted. Alternatively, the heterocycloalkyl group may be substituted.

Unless otherwise specified, the heterocycloalkyl group may be attached at any suitable atom and, if substituted, may be substituted at any suitable atom. Examples of heterocycloalkyl groups include but are not limited to epoxide, morpholinyl, piperadinyl, piperazinyl, thirranyl, pyrrolidinyl, pyrazolidinyl, imidazolidinyl, thiazolidinyl, thiomorpholinyl and the like.

As used herein, the term "heteroaryl" refers to an aromatic carbocyclic group wherein one or more carbon atoms are independently replaced with one or more heteroatoms (e.g. nitrogen, oxygen, phosphorus and/or sulfur atoms). The heteroaryl group may be unsubstituted. Alternatively, the heteroaryl group may be substituted. Unless otherwise specified, the heteroaryl group may be attached at any suitable atom and, if substituted, may be substituted at any suitable atom. Examples of heteroaryl groups include but are not limited to thienyl, furanyl, pyrrolyl, imidazolyl, pyrazolyl, thiazolyl, isothiazolyl, oxazolyl, isoxazolyl, triazolyl, tetrazolyl, thiadiazolyl, thiophenyl, oxadiazolyl, pyridinyl, pyrimidyl, benzoxazolyl, benzthiazolyl, benzimidazolyl, indolyl, quinolinyl and the like.

As used herein, the term "heterocycle" encompasses both heterocycloalkyl groups and heteroaryl groups.

As used herein, the term "substituted" refers to a group in which one or more hydrogen atoms are each independently replaced with substituents (e.g. 1, 2, 3, 4, 5 or more) which may be the same or different. Examples of substituents include but are not limited to -halo, —C(halo)$_3$, —$R^c$, =O, =S, —O—$R^c$, —S—$R^c$, —$NR^cR^d$, —CN, —$NO_2$, —C(O)—$R^c$, —$COOR^d$, —C(S)—$R^c$, —C(S)$OR^d$, —$S(O)_2OH$, —$S(O)_2$—$R^c$, —$S(O)_2NR^cR^d$, —O—S(O)—$R^c$ and —$CONR^cR^d$, such as -halo, —C(halo)$_3$ (e.g. —$CF_3$), —$R^c$, —O—$R^c$, —$NR^cR^d$, —CN, or —$NO_2$. $R^c$ and $R^d$ are independently selected from the groups consisting of H, alkyl, aryl, arylalkyl, heteroalkyl, heteroaryl, or $R^c$ and $R^d$ together with the atom to which they are attached form a heterocycloalkyl group. $R^c$ and $R^d$ may be unsubstituted or further substituted as defined herein.

As used herein, the term "bidentate ligand" refers to a ligand that donates two pairs of electrons to a metal atom.

As used herein, the term "tridentate ligand" refers to a ligand that donates three pairs of electrons to a metal atom.

As used herein, the term "tetradentate ligand" refers to a ligand that donates four pairs of electrons to a metal atom.

As used herein, the term "Ru—SNS" refers to dichlorotriphenylphosphine[bis(2-(ethylthio)ethyl)amine]ruthenium (II).

As used herein, the term "Ru—PNN" refers to dichlorotriphenylphosphine[2-(diphenylphosphino)-N-(2-pyridinylmethyl)ethanamine]ruthenium(II).

As used herein, the term "glycerol ester" refers to an ester formed from glycerol and at least one fatty acid. A glycerol ester formed from glycerol and one fatty acid is also known as a monoglyceride. A glycerol ester formed from glycerol and two fatty acids is also known as a diglyceride. A glycerol ester formed from glycerol and three fatty acids is also known as a triglyceride. The glycerol esters to be hydrogenated in the process of the present invention can be from natural, non-natural, synthetic or semi-synthetic sources. For example, subjection of natural olive oil, which is a composition comprising glycerol esters, to the process of the present invention results in the glycerol esters present therein being directly hydrogenated.

As used herein, the term "fatty acid" refers to a carboxylic acid with a long aliphatic chain (e.g. >6 carbon atoms), which can be either saturated or unsaturated. The aliphatic chain of the fatty acid may be branched or unbranched. In certain embodiments, the aliphatic chain of the fatty acid comprises 12 to 24 carbon atoms. In certain embodiments, the aliphatic chain of the fatty acid comprises 0 to 5 carbon-carbon double bonds.

As used herein, the term "S/C" is an abbreviation for "substrate/catalyst" and is used to describe the catalyst loading employed in a reaction, i.e. it describes the molar ratio of ester(s) and catalyst present in the reaction mixture. In the instance the glycerol ester contains more than one ester moiety, the S/C value is adjusted accordingly. For example, a molar ratio of triglyceride to catalyst of 10,000:1 equates to an S/C of 30,000:1 (as a triglyceride contains three ester moieties).

As used herein, unless otherwise specified, "wt %" describes the weight of the specified material (e.g. a base, a catalyst etc.) relative to the in process weight of the composition comprising a glycerol ester, as a percentage. The "wt %" amount given for the specified material (e.g. a base, a catalyst etc.) is the amount of that material employed in the reaction chamber (i.e. the location where the hydrogenation reaction takes place).

As used herein, the term "turnover number" (TON) refers to the number of moles of substrate that a mole of catalyst can convert before becoming deactivated.

As used herein, the term "neat conditions" is used to describe a reaction which begins with a reaction mixture comprising at least 95% by volume of a mixture of a composition which comprises a glycerol ester and base.

As used herein, the term "hydrogenation" refers to hydrogenation using molecular hydrogen.

As used herein, the term "NMR conversion" refers to the % ratio of hydrogenation product versus total unreacted esters as determined by NMR. For example, an NMR conversion of 89% refers to a reaction mixture containing 89% product alcohol and 11% unreacted esters as determined by NMR.

DETAILED DESCRIPTION

Figure 1:
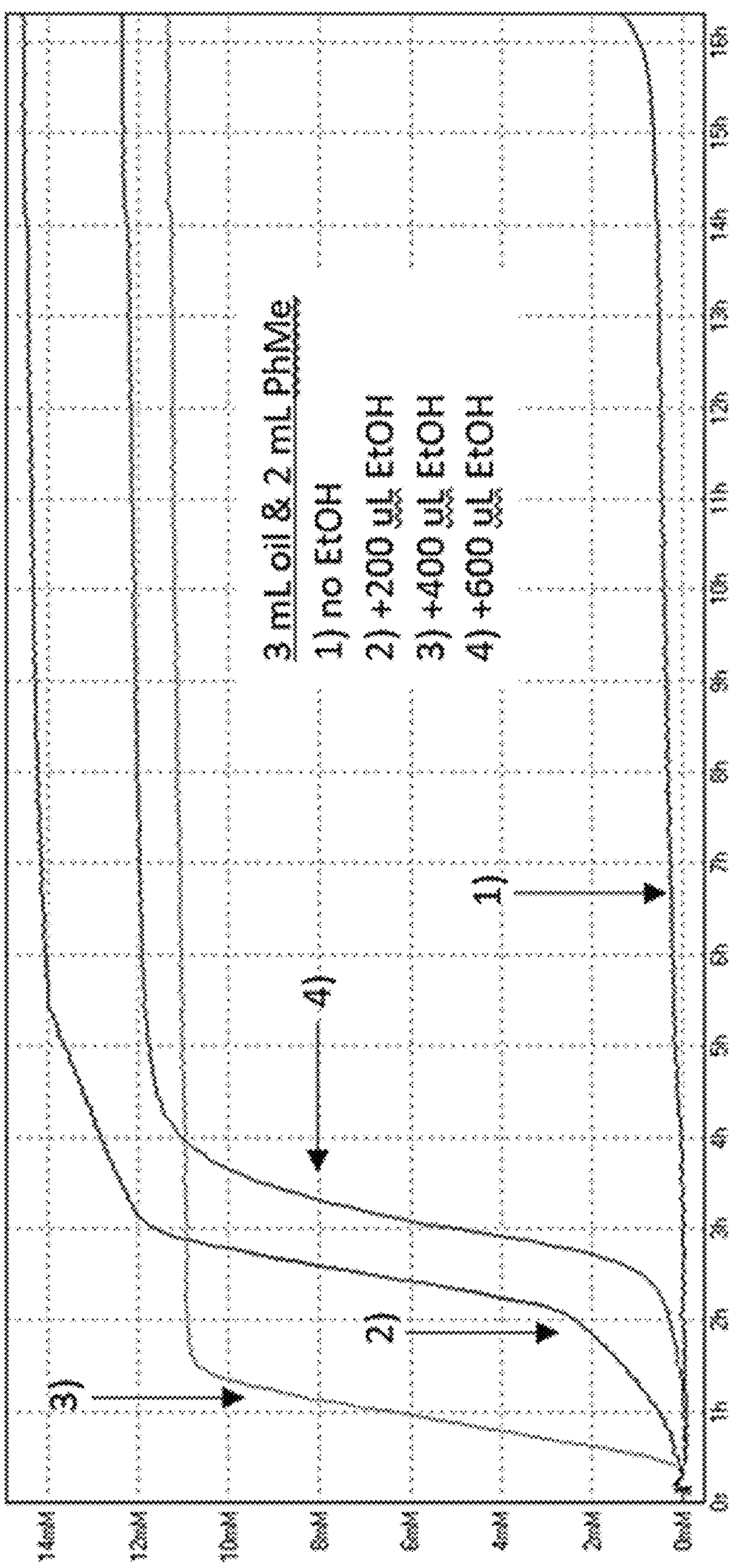
FIG. 1 is a hydrogen uptake curve (i.e. hydrogen uptake in mM (y axis) versus time (x axis)) for the experiments of entries 1-4 of Example 2.

Preferred and/or optional features of the invention will now be set out. Any aspect of the invention may be combined with any other aspect of the invention, unless the context demands otherwise. Any of the preferred or optional features of any aspect of the invention may be combined, singly or in combination, with any aspect of the invention, unless the context demands otherwise.

The present invention provides a process for hydrogenation of a glycerol ester, comprising treating a composition which comprises a glycerol ester with a base and a transition metal catalyst in the presence of molecular hydrogen, wherein the base is present in at least 7 wt % based upon the total weight of said composition and wherein the catalyst is present in less than or equal to 0.05 wt % based upon the total weight of said composition.

In preferred processes of the present invention, the base is present in at least 7.5 wt % based upon the total weight of the composition which comprises a glycerol ester, preferably in at least 8 wt % based upon the total weight of the composition which comprises a glycerol ester, more preferably in at least 8.5 wt % based upon the total weight of the composition which comprises a glycerol ester, even more preferably in at least 9 wt % based upon the total weight of the composition which comprises a glycerol ester, even more preferably in at least 9.5 wt % based upon the total weight of the composition which comprises a glycerol ester, even more preferably in at least 10 wt % based upon the total weight of the composition which comprises a glycerol ester, even more preferably in at least 15 wt % based upon the total weight of the composition which comprises a glycerol ester, even more preferably in at least 20 wt % based upon the total weight of the composition which comprises a glycerol ester, even more preferably in at least 25 wt % based upon the total weight of the composition which comprises a glycerol ester, and even more preferably in at least 30 wt % based upon the total weight of the composition which comprises a glycerol ester. Without wishing to be bound by theory, it is thought that the use of high amounts of base in the processes of the present invention allows for the use of lower catalyst loadings compared to known processes. In some cases, extremely low catalyst loadings have been achieved, e.g. less than or equal to 0.006 wt % catalyst based upon the total weight of the composition which comprises a glycerol ester.

In preferred processes of the present invention, the base is present in less than 50 wt % based upon the total weight of the composition which comprises a glycerol ester, more preferably in less than 45 wt % based upon the total weight of the composition which comprises a glycerol ester, more preferably in less than 40 wt % based upon the total weight of the composition which comprises a glycerol ester, and even more preferably less than 35 wt % based upon the total weight of the composition which comprises a glycerol ester.

In preferred processes of the present invention, the base is present in at least 30 mol % based upon the total amount of glycerol ester, preferably the base is present in at least 35 mol % based upon the total amount of glycerol ester, preferably in at least 40 mol % based upon the total amount of glycerol ester, more preferably in at least 45 mol % based upon the total amount of glycerol ester, even more preferably in at least 50 mol % based upon the total amount of glycerol ester, even more preferably in at least 60 mol % based upon the total amount of glycerol ester, even more preferably in at least 70 mol % based upon the total amount of glycerol ester, even more preferably in at least 80 mol % based upon the total amount of glycerol ester, even more preferably in at least 90 mol % based upon the total amount of glycerol ester, even more preferably in at least 100 mol % based upon the total amount of glycerol ester, and even more preferably in at least 125 mol % based upon the total amount of glycerol ester. Without wishing to be bound by theory, it is thought that the use of high amounts of base in the processes of the present invention allows for the use of lower catalyst loadings compared to known processes. In some cases, extremely low catalyst loadings have been achieved, e.g. S/C=greater than or equal to 40,000/1.

In preferred processes of the present invention, the base is present in less than or equal to 200 mol % based upon the total amount of glycerol ester, more preferably in less than or equal to 175 mol % based upon the total amount of glycerol ester, more preferably in less than or equal to 150 mol % based upon the total amount of glycerol ester, and even more preferably less than or equal to 130 mol % based upon the total amount of glycerol ester.

In preferred processes of the present invention, the base is a metal alkoxide. The metal alkoxide is preferably a metal methoxide, a metal ethoxide, a metal iso-propoxide, or a metal tert-butoxide. Preferred metal alkoxides include lithium ethoxide, sodium ethoxide, potassium ethoxide.

In preferred processes of the present invention, the base is an alkali metal alkoxide. The alkali metal alkoxide is preferably an alkali metal methoxide, an alkali metal ethoxide, an alkali metal iso-propoxide, or an alkali metal tert-butoxide. The alkali metal alkoxide is more preferably an alkali metal methoxide or an alkali metal ethoxide.

In particularly preferred processes of the present invention, the base is an alkali metal ethoxide. The alkali metal ethoxide is preferably lithium ethoxide, sodium ethoxide or potassium ethoxide, more preferably sodium ethoxide.

In preferred processes of the present invention, the base is in solid form.

In preferred processes of the present invention, the base is supported. More preferably, the base is supported on a resin.

In preferred processes of the present invention, the process is carried out in the absence of solvent. This has the advantage of making the process both easier and less expensive to perform.

In alternative preferred processes of the present invention, the process is carried out under neat conditions.

In alternative preferred processes of the present invention, the process is carried out in the presence of at least one solvent.

Preferably, the at least one solvent is selected from an alcohol, toluene, THF and Me-THF. More preferably, the at least one solvent is selected from methanol, ethanol, toluene, THF and Me-THF. Most preferably, the at least one solvent is selected from methanol, ethanol, and toluene.

In some cases, the use of an alcohol solvent, such as ethanol, has been found to minimise the time delay to the starting of the hydrogenation reaction.

In preferred processes of the present invention, the at least one solvent is present in an amount of 10 to 100 vol % based upon the total volume of the composition which comprises a glycerol ester, preferably 15 to 95 vol % based upon the total volume of the composition which comprises a glycerol ester, more preferably 20 to 90 vol % based upon the total volume of the composition which comprises a glycerol ester (e.g. 50 vol % based upon the total volume of the composition which comprises a glycerol ester).

In preferred processes of the present invention, the volume ratio of the at least one solvent to the composition which comprises a glycerol ester is less than or equal to 1:1, preferably less than or equal to 1:2.

In preferred processes of the present invention, the volume ratio of the at least one solvent to the composition which comprises a glycerol ester is in the range 1:2 to 1:1, preferably in the range 1:2 to 1:1.5.

In preferred processes of the present invention, the process is carried out in the presence of more than one solvent. Preferred solvents are as described above.

In alternative preferred processes of the present invention, the process is carried out in the presence of a first solvent and a second solvent.

In preferred processes of the present invention, the first solvent is selected from toluene, THF and Me-THF. In preferred processes of the present invention, the second solvent is an alcohol, preferably ethanol.

In some cases, the use of an alcohol solvent, such as ethanol, as the second solvent has been found to minimise the time delay to starting of the hydrogenation reaction.

In particularly preferred processes of the present invention, the first solvent is toluene and the second solvent is an alcohol, preferably ethanol.

In alternative particularly preferred processes of the present invention, the first solvent is THF and the second solvent is an alcohol, preferably ethanol.

In preferred processes of the present invention, the first solvent is present in an amount of 10 to 100 vol % based upon the total volume of the composition which comprises a glycerol ester, preferably 15 to 95 vol % based upon the total volume of the composition which comprises a glycerol ester, more preferably 20 to 90 vol % based upon the total volume of the composition which comprises a glycerol ester (e.g. 50 vol % based upon the total volume of composition which comprises a glycerol ester).

In preferred processes of the present invention, the volume ratio of the first solvent to the composition which comprises a glycerol ester is less than or equal to 1:1, preferably less than or equal to 1:2.

In preferred processes of the present invention, the volume ratio of the first solvent to the composition which comprises a glycerol ester is in the range 1:2 to 1:1, preferably in the range 1:2 to 1:1.5.

In preferred processes of the present invention, the second solvent is present in an amount of 1 to 15 vol % based upon the total volume of composition which comprises a glycerol ester, preferably in an amount of 1 to 10 vol % based upon the total volume of composition which comprises a glycerol ester, preferably in an amount of 1 to 7.5 vol % based upon the total volume of the composition which comprises a glycerol ester, more preferably in an amount of 1 to 5 vol % based upon the total volume of the composition which comprises a glycerol ester.

In preferred processes of the present invention, the first solvent is present in an amount of 10 to 100 vol % based upon the total volume of the composition which comprises a glycerol ester and the second solvent is present in an amount of 1 to 10 vol % based upon the total volume of the composition which comprises a glycerol ester, preferably the first solvent is present in an amount of 15 to 95 vol % based upon the total volume of the composition which comprises a glycerol ester and the second solvent is present in an amount of 1 to 7.5 vol % based upon the total volume of the composition which comprises a glycerol ester, more preferably the first solvent is present in an amount of 20 to 90 vol % based upon the total volume of the composition which comprises a glycerol ester and the second solvent is present in an amount of 1 to 5 vol % based upon the total volume of the composition which comprises a glycerol ester.

In preferred processes of the present invention, the process is conducted at a temperature in the range 20 to 150° C., more preferably in the range 20 to 140° C., more preferably in the range 25 to 130° C., more preferably in the range 25 to 120° C., more preferably in the range 30 to 100° C., more preferably in the range 30 to 90° C., more preferably in the range 30 to 80° C., more preferably in the range 35 to 75° C., even more preferably in the range 37.5 to 60° C., even more preferably in the range 40 to 55° C., and most preferably in the range 40 to 50° C. (e.g. 40° C.). The preferred processes of the present invention are conducted at relatively low temperatures, meaning that the processes are more economical because the energy input to the reaction is lower. It is thought that lower temperatures for the ester hydrogenation may also help to improve catalyst stability.

Preferred processes of the present invention are conducted at a pressure that is at least 5 bar, more preferably at least 10 bar, even more preferably at least 20 bar, even more preferably at least 30 bar, even more preferably at least 40 bar, and most preferably at least 50 bar.

Preferred processes of the present invention are conducted at a pressure that is in the range 5 to 100 bar, more preferably in the range 10 to 95 bar, even more preferably in the range 20 to 90 bar, even more preferably in the range 25 to 70 bar, and most preferably in the range 30 to 50 bar.

Preferred processes of the present invention are conducted for a duration of 1 to 24 hours, more preferably 2 to 16 hours, even more preferably 3 to 10 hours, and most preferably 4 to 8 hours.

The processes of the present invention require a low catalyst loading, whilst still achieving an industrially useful TON and conversion for the ester hydrogenation. A lower catalyst loading means that the reactions are greener and more efficient. A lower catalyst loading also means that the cost of the reaction can be reduced.

In the process of the present invention, the catalyst is present in less than or equal to 0.05 wt % based upon the total weight of the composition which comprises a glycerol ester. In preferred processes of the present invention, the catalyst is present in less than or equal to 0.04 wt % based upon the total weight of the composition which comprises a glycerol ester, more preferably less than or equal to 0.03 wt % based upon the total weight of the composition which comprises a glycerol ester, even more preferably less than or equal to 0.02 wt % based upon the total weight of the composition which comprises a glycerol ester, even more preferably less than or equal to 0.01 wt % based upon the total weight of the composition which comprises a glycerol ester, even more preferably less than or equal to 0.009 wt % based upon the total weight of the composition which comprises a glycerol ester, even more preferably less than or equal to 0.008 wt % based upon the total weight of the composition which comprises a glycerol ester, even more preferably less than or equal to 0.007 wt % based upon the total weight of the composition which comprises a glycerol ester, even more preferably less than or equal to 0.006 wt % based upon the total weight of the composition which comprises a glycerol ester, even more preferably less than or equal to 0.005 wt % based upon the total weight of the composition which comprises a glycerol ester, even more preferably less than or equal to 0.004 wt % based upon the total weight of the composition which comprises a glycerol ester, even more preferably less than or equal to 0.003 wt % based upon the total weight of the composition which comprises a glycerol ester, even more preferably less than or equal to 0.002 wt % based upon the total weight of the composition which comprises a glycerol ester, even more preferably less than or equal to 0.001 wt % based upon the total weight of the composition which comprises a glycerol ester, even more preferably less than or equal to 0.0009 wt % based upon the total weight of the composition which comprises a glycerol ester, even more preferably less than or equal to 0.0008 wt % based upon the total weight of the composition which comprises a glycerol ester, even more preferably less than or equal to 0.0007 wt % based upon the total weight of the composition which comprises a glycerol ester, even more preferably less than or equal to 0.0006 wt % based upon the total weight of the composition which comprises a glycerol ester, and even more preferably less than or equal to 0.0005 wt % based upon the total weight of the composition which comprises a glycerol ester.

In some embodiments of the process of the present invention, the catalyst is present in more than or equal to 0.0004 wt % based upon the total weight of the composition which comprises a glycerol ester.

In the process of the present invention, the substrate/catalyst (S/C) loading is greater than or equal to 5,000/1. In preferred processes of the present invention, the substrate/catalyst loading is greater than or equal to 6,000/1, more preferably greater than or equal to 7,000/1, more preferably greater than or equal to 8,000/1, even more preferably greater than or equal to 9,000/1, more preferably greater than or equal to 10,000/1, even more preferably greater than or equal to 15,000/1, even more preferably greater than or equal to 20,000/1, even more preferably greater than or equal to 30,000/1, even more preferably greater than or equal to 40,000/1, even more preferably greater than or equal to 50,000/1, even more preferably greater than or equal to 60,000/1, even more preferably greater than or equal to 70,000/1, even more preferably greater than or equal to 80,000/1, even more preferably greater than or equal to 90,000/1, even more preferably greater than or equal to 100,000/1, even more preferably greater than or equal to 200,000/1, even more preferably greater than or equal to 300,000/1, even more preferably greater than or equal to 400,000/1.

In some embodiments of the process of the present invention, the substrate/catalyst loading is less than or equal to 500,000/1.

The process of the present invention employs a transition metal catalyst. The transition metal catalyst may be pre-formed or may be formed in situ during the ester hydrogenation reaction. Preferably, the transition metal catalyst is pre-formed. Alternatively, the transition metal catalyst is formed in situ during the ester hydrogenation reaction.

In preferred processes of the present invention, the transition metal in the transition metal catalyst is a Group 6, Group 7, Group 8, or Group 9 transition metal. More preferably, the transition metal in the transition metal catalyst is a Group 7, Group 8, or Group 9 transition metal. Even more preferably, the transition metal in the transition metal catalyst is a Group 8 transition metal.

In preferred processes of the present invention, the transition metal in the transition metal catalyst is selected from Mo, Mn, Fe, Ru, Co and Os. More preferably, the transition metal in the transition metal catalyst is selected from Ru and Os. Most preferably, the transition metal in the transition metal catalyst is Ru.

In preferred processes of the present invention, the transition metal catalyst employed in the process of the present invention comprises a tridentate ligand.

In preferred processes of the present invention, the transition metal catalyst comprises a tridentate ligand having a Formula (I)

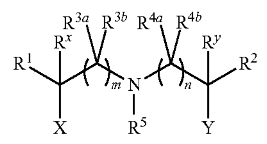

(I)

wherein:

X is selected from —$SR^a$, —$OR^a$, —$CR^a$, —$NR^aR^b$, —$PR^aR^b$, —$P(=O)R^aR^b$, —$OPR^aR^b$, and —$NHPR^aR^b$;

$R^1$ and $R^x$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl, or $R^1$ and one of $R^{3a}$ and $R^{3b}$ or $R^x$ and one of $R^{3a}$ and $R^{3b}$ together with the atoms to which they are bound, form a ring;

or X is a heteroatom and when taken together with $R^1$ it forms an optionally substituted heterocycle when $R^x$ is absent;

Y is selected from —$SR^a$, —$OR^a$, —$CR^a$, —$NR^aR^b$, —$PR^aR^b$, —$P(=O)R^aR^b$, —$OPR^aR^b$, and —$NHPR^aR^b$;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl, or $R^2$ and one of $R^{4a}$ and $R^{4b}$ or $R^y$ and one of $R^{4a}$ and $R^{4b}$ together with the atoms to which they are bound, form a ring;

or Y is a heteroatom and when taken together with $R^2$ it forms an optionally substituted heterocycle when $R^y$ is absent;

$R^{3a}$, $R^{3b}$, $R^{4a}$, and $R^{4b}$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl, or $R^{3a}$ and one of $R^{4a}$ and $R^{4b}$ or $R^{3b}$ and one of $R^{4a}$ and $R^{4b}$ together with the atoms to which they are bound, form a heterocycle;

$R^5$ is selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ and $R^b$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or when X and/or Y is —$NR^aR^b$, —$PR^aR^b$, —$OPR^aR^b$, or —$NHPR^aR^b$, $R^a$ and $R^b$ together with the heteroatom to which they are attached form a heterocycle.

In tridentate ligands of Formula (I), X is preferably selected from —$SR^a$, —$CR^a$, —$NR^aR^b$, —$PR^aR^b$, and —$NHPR^aR^b$. More preferably, X is selected from —$SR^a$, —$PR^aR^b$, and —$NHPR^aR^b$. Even more preferably, X is selected from —$SR^a$ and —$PR^aR^b$. Most preferably, X is —$SR^a$.

In tridentate ligands of Formula (I), $R^1$ and $R^x$ are each independently preferably selected from hydrogen, substituted or unsubstituted $C_{1-20}$-alkyl, substituted or unsubstituted $C_{1-20}$-heteroalkyl and substituted or unsubstituted $C_{3-20}$-cycloalkyl. More preferably, $R^1$ and $R^x$ are each independently selected from hydrogen and substituted or unsubstituted $C_{1-20}$-alkyl. Even more preferably, $R^1$ and $R^x$ are each hydrogen.

In alternative preferred tridentate ligands of Formula (I), X is a heteroatom and when taken together with $R^1$ it forms an optionally substituted heterocycle when $R^x$ is absent. More preferably, X is a heteroatom and when taken together with $R^1$ it forms an optionally substituted heteroaromatic ring when $R^x$ is absent. More preferably, the optionally substituted heteroaromatic ring is an optionally substituted nitrogen-containing heteroaromatic ring. Even more preferably, the optionally substituted nitrogen-containing heteroaromatic ring is selected from pyridinyl, pyrrolyl, imidazolyl, pyrazolyl, thiazolyl, isothiazolyl, oxazolyl, isoxazolyl, triazolyl, tetrazolyl, thiadiazolyl, oxadiazolyl, pyrimidyl, benzoxazolyl, benzthiazolyl, benzimidazolyl, indolyl, and quinolinyl. Even more preferably, the optionally substituted nitrogen-containing heteroaromatic ring is selected from pyridinyl, pyrrolyl, imidazolyl, pyrazolyl, triazolyl, tetrazolyl, and pyrimidyl. Most preferably, the optionally substituted nitrogen-containing heteroaromatic ring is pyridinyl.

In tridentate ligands of Formula (I), Y is preferably selected from —$SR^a$, —$CR^a$, —$NR^aR^b$, —$PR^aR^b$, and —$NHPR^aR^b$. More preferably, Y is selected from —$SR^a$, —$PR^aR^b$, and —$NHPR^aR^b$. Even more preferably, Y is selected from —$SR^a$ and —$PR^aR^b$. Most preferably, Y is —$SR^a$.

In tridentate ligands of Formula (I), $R^2$ and $R^y$ are each independently preferably selected from hydrogen, substituted or unsubstituted $C_{1-20}$-alkyl, substituted or unsubstituted $C_{1-20}$-heteroalkyl and substituted or unsubstituted $C_{3-20}$-cycloalkyl. More preferably, $R^2$ and $R^y$ are each independently selected from hydrogen and substituted or unsubstituted $C_{1-20}$-alkyl. Even more preferably, $R^2$ and $R^y$ are each hydrogen.

In alternative preferred tridentate ligands of Formula (I), Y is a heteroatom and when taken together with $R^2$ it forms an optionally substituted heterocycle when $R^y$ is absent. More preferably, Y is a heteroatom and when taken together with $R^2$ it forms an optionally substituted heteroaromatic ring when $R^y$ is absent. More preferably, the optionally substituted heteroaromatic ring is an optionally substituted nitrogen-containing heteroaromatic ring. Even more preferably, the optionally substituted nitrogen-containing heteroaromatic ring is selected from pyridinyl, pyrrolyl, imidazolyl, pyrazolyl, thiazolyl, isothiazolyl, oxazolyl, isoxazolyl, triazolyl, tetrazolyl, thiadiazolyl, oxadiazolyl, pyrimidyl, benzoxazolyl, benzthiazolyl, benzimidazolyl, indolyl, and quinolinyl. Even more preferably, the optionally substituted nitrogen-containing heteroaromatic ring is selected from pyridinyl, pyrrolyl, imidazolyl, pyrazolyl, triazolyl, tetrazolyl, and pyrimidyl. Most preferably, the optionally substituted nitrogen-containing heteroaromatic ring is pyridinyl.

In tridentate ligands of Formula (I), $R^{3a}$, $R^{3b}$, $R^{4a}$, and $R^{4b}$ are each independently preferably selected from hydrogen, substituted or unsubstituted $C_{1-20}$-alkyl, substituted or unsubstituted $C_{1-20}$-heteroalkyl and substituted or unsubstituted $C_{3-20}$-cycloalkyl. More preferably, $R^{3a}$, $R^{3b}$, $R^{4a}$, and $R^{4b}$ are each independently selected from hydrogen and substituted or unsubstituted $C_{1-20}$-alkyl. Even more preferably, $R^{3a}$, $R^{3b}$, $R^{4a}$, and $R^{4b}$ are each hydrogen.

In alternative preferred tridentate ligands of Formula (I), $R^{3a}$ and one of $R^{4a}$ and $R^{4b}$ or $R^{3b}$ and one of $R^{4a}$ and $R^{4b}$ together with the atoms to which they are bound, form a heterocycle. Preferably, the heterocycle is a six-membered ring heterocycle.

In tridentate ligands of Formula (I), $R^5$ is preferably selected from hydrogen, substituted or unsubstituted $C_{1-20}$-alkyl, substituted or unsubstituted $C_{1-20}$-heteroalkyl and substituted or unsubstituted $C_{3-20}$-cycloalkyl. More preferably, $R^5$ is selected from hydrogen and substituted or unsubstituted $C_{1-20}$-alkyl. Even more preferably, $R^5$ is hydrogen.

In tridentate ligands of Formula (I), each m and n is preferably 1.

In tridentate ligands of Formula (I), $R^a$ and $R^b$, if present, are each independently preferably selected from hydrogen, substituted or unsubstituted $C_{1-20}$-alkyl, substituted or unsubstituted $C_{1-20}$-heteroalkyl, substituted or unsubstituted $C_{3-20}$-cycloalkyl, substituted or unsubstituted $C_{6-20}$-aryl, and substituted or unsubstituted $C_{4-20}$-heteroaryl. More preferably, $R^a$ and $R^b$, if present, are each independently selected from hydrogen, substituted or unsubstituted $C_{1-20}$-alkyl (e.g. $C_{1-10}$-alkyl) and substituted or unsubstituted $C_{6-20}$-aryl. Particularly preferred $C_{1-20}$-alkyl groups include ethyl, ethyl, n-propyl, iso-propyl, n-butyl, sec-butyl, tert-butyl, pentyl, and hexyl, more preferably methyl, ethyl, iso-propyl, tert-butyl, even more preferably ethyl. Preferred $C_{6-20}$-aryl groups include phenyl, tolyl, xylyl, and methoxyphenyl, more preferably phenyl.

In alternative preferred tridentate ligands of Formula (I), when X and/or Y is —$NR^aR^b$, —$PR^aR^b$, —$OPR^aR^b$, or —$NHPR^aR^b$, $R^a$ and $R^b$ together with the heteroatom to which they are attached form a heterocycle.

In preferred processes of the present invention, the transition metal catalyst comprises a tridentate ligand having a Formula (I)

wherein:

X is selected from —$SR^a$, —$CR^a$, —$NR^aR^b$, —$PR^aR^b$, and —$NHPR^aR^b$—;

$R^1$ and $R^x$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or X is a heteroatom and when taken together with $R^1$ it forms an optionally substituted heteroaromatic ring when $R^x$ is absent, wherein the heteroaromatic ring is a nitrogen-containing heteroaromatic ring;

Y is selected from —$SR^a$, —$CR^a$, —$NR^aR^b$, —$PR^aR^b$, and —$NHPR^aR^b$—;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or Y is a heteroatom and when taken together with $R^2$ it forms an optionally substituted heteroaromatic ring when $R^y$ is absent, wherein the heteroaromatic ring is a nitrogen-containing heteroaromatic ring;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ and $R^b$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or when X and/or Y is —$NR^aR^b$, —$PR^aR^b$ or —$NHPR^aR^b$, $R^a$ and $R^b$ together with the heteroatom to which they are attached form a heterocycle.

In preferred processes of the present invention, the transition metal catalyst comprises a tridentate ligand having a Formula (I)

wherein:

X is selected from —$SR^a$, —$PR^aR^b$, and —$NHPR^aR^b$;

$R^1$ and $R^x$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or X is a heteroatom and when taken together with $R^1$ it forms an optionally substituted heteroaromatic ring when $R^x$ is absent, wherein the heteroaromatic ring is a nitrogen-containing heteroaromatic ring selected from pyridinyl, pyrrolyl, imidazolyl, pyrazolyl, thiazolyl, isothiazolyl, oxazolyl, isoxazolyl, triazolyl, tetrazolyl, thiadiazolyl, oxadiazolyl, pyrimidyl, benzoxazolyl, benzthiazolyl, benzimidazolyl, indolyl, and quinolinyl;

Y is selected from —$SR^a$, —$PR^aR^b$, and —$NHPR^aR^b$;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or Y is a heteroatom and when taken together with $R^2$ it forms an optionally substituted heteroaromatic ring when $R^y$ is absent, wherein the heteroaromatic ring is a nitrogen-containing heteroaromatic ring selected from pyridinyl, pyrrolyl, imidazolyl, pyrazolyl, thiazolyl, isothiazolyl, oxazolyl, isoxazolyl, triazolyl, tetrazolyl, thiadiazolyl, oxadiazolyl, pyrimidyl, benzoxazolyl, benzthiazolyl, benzimidazolyl, indolyl, and quinolinyl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ and $R^b$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or when X and/or Y is —$PR^aR^b$ or —$NHPR^aR^b$, $R^a$ and $R^b$ together with the heteroatom to which they are attached form a heterocycle.

In preferred processes of the present invention, the transition metal catalyst comprises a tridentate ligand having a Formula (I)

wherein:

X is selected from —$SR^a$ and —$PR^aR^b$;

$R^1$ and $R^x$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or X is a heteroatom and when taken together with $R^1$ it forms an optionally substituted heteroaromatic ring when $R^x$ is absent, wherein the heteroaromatic ring is a nitrogen-containing heteroaromatic ring selected from pyridinyl, pyrrolyl, imidazolyl, pyrazolyl, triazolyl, tetrazolyl, and pyrimidyl;

Y is selected from —$SR^a$ and —$PR^aR^b$;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or Y is a heteroatom and when taken together with $R^2$ it forms an optionally substituted heteroaromatic ring when $R^y$ is absent, wherein the heteroaromatic ring is a nitrogen-containing heteroaromatic ring selected from pyridinyl, pyrrolyl, imidazolyl, pyrazolyl, triazolyl, tetrazolyl, and pyrimidyl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ and $R^b$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or when X and/or Y is —$PR^aR^b$, $R^a$ and $R^b$ together with the heteroatom to which they are attached form a heterocycle.

In preferred processes of the present invention, the transition metal catalyst comprises a tridentate ligand having a Formula (I), wherein:

X is —$SR^a$;

$R^1$ and $R^x$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

Y is —$SR^a$;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl.

Preferably, the transition metal catalyst comprises a tridentate ligand having a Formula (I), wherein:

X is —$SR^a$;

$R^1$ and $R^x$ are each independently selected from hydrogen, substituted or unsubstituted $C_{1-20}$-alkyl, substituted or unsubstituted $C_{1-20}$-heteroalkyl, and substituted or unsubstituted $C_{3-20}$-cycloalkyl;

Y is —$SR^a$;

$R^2$ and $R^y$ are each independently selected from hydrogen, substituted or unsubstituted $C_{1-20}$-alkyl, substituted or unsubstituted $C_{1-20}$-heteroalkyl, and substituted or unsubstituted $C_{3-20}$-cycloalkyl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{1-20}$-heteroalkyl, and substituted or unsubstituted $C_{3-20}$-cycloalkyl;

each m and n is independently 1 or 2; and $R^a$ are each independently selected from hydrogen, substituted or unsubstituted $C_{1-20}$-alkyl, substituted or unsubstituted $C_{1-20}$-heteroalkyl, and substituted or unsubstituted $C_{3-20}$-cycloalkyl.

More preferably, the transition metal catalyst comprises a tridentate ligand having a Formula (I), wherein:

X is —$SR^a$;

$R^1$ and $R^x$ are each independently selected from hydrogen and substituted or unsubstituted $C_{1-20}$-alkyl;

Y is —$SR^a$;

$R^2$ and $R^y$ are each independently selected from hydrogen and substituted or unsubstituted $C_{1-20}$-alkyl;

$R^{3a}$, $R^{3b}$, $R^{4a}$, $R^{4b}$ and $R^5$ are each independently selected from hydrogen and substituted or unsubstituted $C_{1-20}$-alkyl;

each m and n is independently 1 or 2; and $R^a$ are each independently selected from hydrogen and substituted or unsubstituted $C_{1-20}$-alkyl, substituted or unsubstituted $C_{1-20}$-heteroalkyl, and substituted or unsubstituted $C_{3-20}$-cycloalkyl.

Even more preferably, the transition metal catalyst comprises a tridentate ligand having a Formula (I), wherein:

X and Y are each —$SR^a$;

$R^1$, $R^x$, $R^2$, $R^y$, $R^{3a}$, $R^{3b}$, $R^{4a}$, $R^{4b}$ and $R^5$ are each hydrogen;

m and n are each 1; and $R^a$ are each independently substituted or unsubstituted $C_{1-20}$-alkyl, preferably $C_{1-10}$ alkyl.

Even more preferably, the transition metal catalyst comprises a tridentate ligand having a Formula (I), wherein:

X and Y are each —SEt;

$R^1$, $R^x$, $R^2$, $R^y$, $R^{3a}$, $R^{3b}$, $R^{4a}$, $R^{4b}$ and $R^5$ are each hydrogen; and m and n are each 1.

In alternative preferred processes of the present invention, the transition metal catalyst comprises a tridentate ligand having a Formula (I), wherein:

X is a heteroatom and when taken together with $R^1$ it forms an optionally substituted heteroaromatic ring when $R^x$ is absent;

Y is —$PR^aR^b$;

$R^2$ and $R^y$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each m and n is independently 1 or 2; and $R^a$ and $R^b$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or $R^a$ and $R^b$ together with the heteroatom to which they are attached form a heterocycle.

Preferably, the transition metal catalyst comprises a tridentate ligand having a Formula (I), wherein:

X is a nitrogen atom and when taken together with $R^1$ it forms an optionally substituted heteroaromatic ring when $R^x$ is absent, wherein the heteroaromatic ring is a nitrogen-containing heteroaromatic ring;

Y is —$PR^aR^b$;

$R^2$ and $R^y$ are each independently is selected from hydrogen, substituted or unsubstituted $C_{1-20}$-alkyl, substituted or unsubstituted $C_{1-20}$-heteroalkyl, and substituted or unsubstituted $C_{3-20}$-cycloalkyl;

$R^{3a}$, $R^{3b}$, $R^{4a}$, $R^{4b}$ and $R^5$ are each independently selected from hydrogen, substituted or unsubstituted $C_{1-20}$-alkyl, substituted or unsubstituted $C_{1-20}$-heteroalkyl, substituted or unsubstituted $C_{3-20}$-cycloalkyl;

each m and n is independently 1 or 2; and $R^a$ and $R^b$ are each independently selected from substituted or unsubstituted $C_{1-20}$-alkyl, substituted or unsubstituted $C_{1-20}$-heteroalkyl, substituted or unsubstituted $C_{3-20}$-cycloalkyl, substituted or unsubstituted $C_{6-20}$-aryl, and substituted or unsubstituted $C_{4-20}$-heteroaryl.

More preferably, the transition metal catalyst comprises a tridentate ligand having a Formula (I), wherein:

X is a nitrogen atom and when taken together with $R^1$ it forms an optionally substituted heteroaromatic ring when $R^x$ is absent, wherein the heteroaromatic ring is a nitrogen-containing heteroaromatic ring selected from pyridinyl, pyrrolyl, imidazolyl, pyrazolyl, thiazolyl, isothiazolyl, oxazolyl, isoxazolyl, triazolyl, tetrazolyl, thiadiazolyl, oxadiazolyl, pyrimidyl, benzoxazolyl, benzthiazolyl, benzimidazolyl, indolyl, and quinolinyl;

Y is —$PR^aR^b$;

$R^2$, $R^y$, $R^{3a}$, $R^{3b}$, $R^{4a}$, $R^{4b}$ and $R^5$ are each hydrogen;

each m and n is 1; and $R^a$ and $R^b$ are each independently selected from substituted or unsubstituted $C_{1-20}$-alkyl and substituted or unsubstituted $C_{6-20}$-aryl.

Even more preferably, the transition metal catalyst comprises a tridentate ligand having a Formula (I), wherein:

X is a nitrogen atom and when taken together with $R^1$ it forms an optionally substituted heteroaromatic ring when $R^x$ is absent, wherein the heteroaromatic ring is a nitrogen-containing heteroaromatic ring selected from pyridinyl, pyrrolyl, imidazolyl, pyrazolyl, triazolyl, tetrazolyl, and pyrimidyl;

Y is —$PR^aR^b$;

$R^2$, $R^y$, $R^{3a}$, $R^{3b}$, $R^{4a}$, $R^{4b}$ and $R^5$ are each hydrogen;

each m and n is 1; and $R^a$ and $R^b$ are each independently selected from methyl, ethyl, n-propyl, iso-propyl, n-butyl, sec-butyl, tert-butyl, pentyl, hexyl, phenyl, tolyl, xylyl, and methoxyphenyl.

Even more preferably, the transition metal catalyst comprises a tridentate ligand having a Formula (I), wherein:

X is a nitrogen atom and when taken together with $R^1$ it forms an optionally substituted pyridinyl ring when $R^x$ is absent;

Y is —$PR^aR^b$;

$R^2$, $R^y$, $R^{3a}$, $R^{3b}$, $R^{4a}$, $R^{4b}$ and $R^5$ are each hydrogen;

each m and n is 1; and $R^a$ and $R^b$ are each independently selected from methyl, ethyl, iso-propyl, tert-butyl, phenyl, tolyl, xylyl, and methoxyphenyl.

Even more preferably, the transition metal catalyst comprises a tridentate ligand having a Formula (I), wherein:

X is a nitrogen atom and when taken together with $R^1$ it forms an optionally substituted pyridinyl ring when $R^x$ is absent;

Y is —$PR^aR^b$;

$R^2$, $R^y$, $R^{3a}$, $R^{3b}$, $R^{4a}$, $R^{4b}$ and $R^5$ are each hydrogen;

each m and n is 1; and $R^a$ and $R^b$ are each phenyl.

In preferred processes of the present invention, the transition metal catalyst has a Formula (II) or Formula (III)

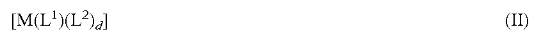

$$[M(L^1)(L^2)_d] \quad \text{(II)}$$

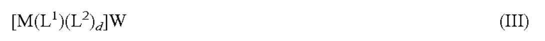

$$[M(L^1)(L^2)_d]W \quad \text{(III)}$$

wherein:

M is a transition metal;

$L^1$ is a tridentate ligand as hereinbefore defined;

$L^2$ are ligands which may be the same or different;

d is 1, 2 or 3; and

W is a non-coordinated anionic ligand.

In preferred processes of the present invention, M is a Group 6, Group 7, Group 8, or Group 9 transition metal. More preferably, M is a Group 7, Group 8, or Group 9 transition metal. Even more preferably, M is a Group 8 transition metal.

In preferred processes of the present invention, M is a transition metal selected from Mo, Mn, Fe, Co, Ru, and Os. More preferably, M is a transition metal selected from Ru and Os. Most preferably, M is Ru.

In preferred processes of the present invention, d is 3.

As will be understood by a skilled person, each $L^2$ may be a monodentate ligand or a multidentate ligand, provided the combination of $L^2$ ligands is allowed by the rules of valency. In preferred processes of the present invention, each $L^2$ is a monodentate ligand. Preferably, each $L^2$ is independently a neutral monodentate ligand or an anionic monodentate ligand. In preferred processes of the present invention, each $L^2$ is independently selected from —H, —CO, —CN, —$P(R')_3$, —$As(R')_3$, —CR', —OR', —O(C═O)R', —$NR'_2$, halogen (e.g. —Cl, —Br, —I), and solvent, wherein each R' is independently selected from substituted or unsubstituted alkyl, substituted or unsubstituted alkenyl, substituted or unsubstituted alkynyl, substituted or unsubstituted heteroalkyl, substituted or unsubstituted alkoxy, substituted or unsubstituted cycloalkyl, substituted or unsubstituted heterocycloalkyl, substituted or unsubstituted aryl, and substituted or unsubstituted heteroaryl. Preferably, each $L^2$ is independently selected from —H, —CO, —P(R')$_3$, and halogen. More preferably, each $L^2$ is independently selected from —CO, —$PPh_3$, and —Cl. When $L^2$ is solvent, the solvent is preferably selected from THF, Me-THF, MeCN, $H_2O$ and an alcohol (e.g. methanol, ethanol, iso-propanol etc.).

In the transition metal catalysts of formula (III), W is a non-coordinated anionic ligand. By "non-coordinated anion ligand", we mean the anionic ligand is forced to the outer sphere of the metal centre. The anionic ligand, therefore, is dissociated from the metal centre. This is in contrast to neutral complexes in which the anionic ligand is bound to the metal within the coordination sphere. The anionic ligand can be generally identified as non-coordinating by analysing the X-ray crystal structure of the cationic complex. Preferably, W is selected from the group consisting of triflate (i.e. $TfO^-$ or $CF_3SO_3^-$), tetrafluoroborate (i.e. $^-BF_4$), hexafluoroantimonate (i.e. $^-SbF_6$), hexafluorophosphate ($PF_6^-$), $[B[3,5-(CF_3)_2C_6H_3]_4]^-$ ($[BAr^F_4]^-$), halide (e.g. $Cl^-$, $Br^-$, $I^-$) and mesylate ($MsO^-$ or $MeSO_3^-$).

Preferably, the transition metal catalyst is a transition metal catalyst of Formula (II).

Alternatively, the transition metal catalyst is a transition metal catalyst of Formula (III).

In preferred processes of the present invention, the transition metal catalyst is

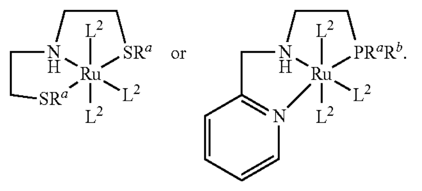

In preferred processes of the present invention, the transition metal catalyst is Ru—SNS or Ru—PNN.

In preferred processes of the present invention, the transition metal catalyst is

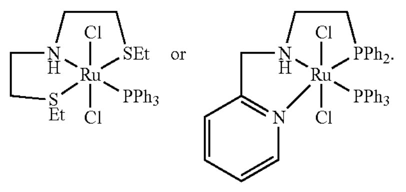

In preferred processes of the present invention, the transition metal catalyst employed in the processes of the present invention comprises a bidentate ligand.

In preferred processes of the present invention, the transition metal catalyst comprises a bidentate ligand having a Formula (IV)

(IV)

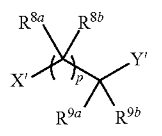

wherein:

X' is —$NHR^{ax}$;

Y' is selected from —$SR^{ax}$, —$OR^{ax}$, —$CR^{ax}$, —$NR^{ax}R^{bx}$, —$PR^{ax}R^{bx}$, —P(═O)$R^{ax}R^{bx}$, —$OPR^{ax}R^{bx}$, and —NH-$PR^{ax}R^{bx}$;

$R^{8a}$, $R^{8b}$, $R^{9a}$ and $R^{9b}$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

p is 1 or 2; and $R^{ax}$ and $R^{bx}$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or when X' and/or Y' is —$NR^{ax}R^{bx}$, —$PR^{ax}R^{bx}$, —$OPR^{ax}R^{bx}$, or —$NHPR^{ax}R^{bx}$, $R^{ax}$ and $R^{bx}$ together with the heteroatom to which they are attached form a heterocycle.

In preferred processes of the present invention, the transition metal catalyst has a Formula (V) or Formula (VI)

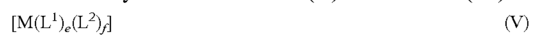

$[M(L^1)_e(L^2)_f]$ (V)

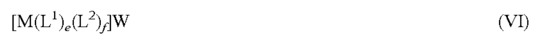

$[M(L^1)_e(L^2)_f]W$ (VI)

wherein:

M is a transition metal;

$L^1$ are bidentate ligands as hereinbefore defined which may be the same or different;

$L^2$, if present, are ligands which may be the same or different;

e is 1 or 2 such that when e is 1, f is 2, 3 or 4, and when e is 2, f is 0, 1 or 2; and W is a non-coordinated anionic ligand.

M, $L^2$ and W are as generally described above.

In preferred processes of the present invention, the transition metal catalyst employed in the processes of the present invention comprises a tetradentate ligand.

In preferred processes of the present invention, the transition metal catalyst comprises a tetradentate ligand having a Formula (VII)

(VII)

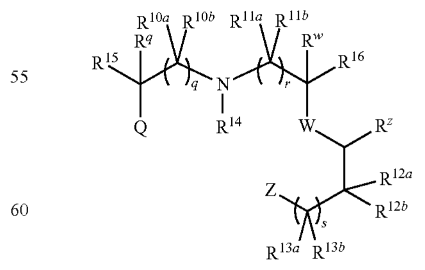

wherein:

Q is selected from —$SR^{ay}$, —$OR^{ay}$, —$CR^{ay}$, —$NR^{ay}R^{by}$, —$PR^{ay}R^{by}$, —P(═O)$R^{ay}R^{by}$, —$OPR^{ay}R^{by}$, and —$NHPR^{ay}$-$R^{by}$;

$R^{15}$ and $R^q$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or Q is a heteroatom and when taken together with $R^{15}$ it forms an optionally substituted heterocycle when $R^q$ is absent;

W is selected from S, O, $NR^a$, and $PR^a$;

$R^{16}$, $R^w$ and $R^z$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

or $R^{16}$ when taken together with $R^z$ forms an optionally substituted heterocycle when $R^w$ is absent;

Z is selected from $—SR^{ay}$, $—OR^{ay}$, $—CR^{ay}$, $—NR^{ay}R^{by}$, $—PR^{ay}R^{by}$, $—P(=O)R^{ay}R^{by}$, $—OPR^{ay}R^{by}$, and $—NHPR^{ay}R^{by}$;

$R^{10a}$, $R^{10b}$, $R^{11a}$, and $R^{11b}$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or $R^{10a}$ and one of $R^{11a}$ and $R^{11b}$ or $R^{10b}$ and one of $R^{11a}$ and $R^{11b}$ together with the atoms to which they are bound, form a heterocycle;

$R^{12a}$, $R^{12b}$, $R^{13a}$, $R^{13b}$ and $R^{14}$ are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl;

each q and r is independently 1 or 2;

s is 0, 1 or 2; and $R^{ay}$ and $R^{by}$, if present, are each independently selected from hydrogen, substituted or unsubstituted $C_{1-20}$-alkyl, substituted or unsubstituted $C_{2-20}$-alkenyl, substituted or unsubstituted $C_{2-20}$-alkynyl, substituted or unsubstituted $C_{1-20}$-heteroalkyl, substituted or unsubstituted $C_{1-20}$-alkoxy, substituted or unsubstituted $C_{3-20}$-cycloalkyl, substituted or unsubstituted $C_{3-20}$-cycloalkenyl, substituted or unsubstituted $C_{2-20}$-heterocycloalkyl, substituted or unsubstituted $C_{6-20}$-aryl, and substituted or unsubstituted $C_{4-20}$-heteroaryl; or when Q and/or Z is $—NR^{ay}R^{by}$, $—PR^{ay}R^{by}$, $—OPR^{ay}R^{by}$, or $—NHPR^{ay}R^{by}$, $R^{ay}$ and $R^{by}$ together with the heteroatom to which they are attached form a heterocycle.

In preferred processes of the present invention, the transition metal catalyst has a Formula (VIII) or Formula (IX)

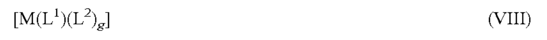

$$[M(L^1)(L^2)_g] \quad \text{(VIII)}$$

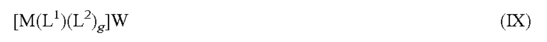

$$[M(L^1)(L^2)_g]W \quad \text{(IX)}$$

wherein:

M is a transition metal;

$L^1$ is a tetradentate ligand as hereinbefore defined;

$L^2$, if present, are ligands which may be the same or different;

g is 0, 1 or 2; and

W is a non-coordinated anionic ligand.

M, $L^2$ and W are as generally described above.

In preferred processes of the present invention, the transition metal catalyst is removed from the reaction mixture by a precipitation step using a co-solvent.

In alternative preferred processes of the present invention, the transition metal catalyst is removed from the reaction mixture by distillation of the product.

In alternative preferred processes of the present invention, the transition metal catalyst is removed from the reaction mixture by crystallisation of the product.

In alternative preferred processes of the present invention, the transition metal catalyst is removed from the reaction mixture using a metal scavenger.

In preferred processes of the present invention, said treating of said composition which comprises a glycerol ester with a base and a transition metal catalyst in the presence of molecular hydrogen hydrogenates said glycerol ester.

In preferred processes of the present invention, said composition comprises a mixture of glycerol esters.

In preferred processes of the present invention, said composition consists of a glycerol ester.

In preferred processes of the present invention, said composition consists of a mixture of glycerol esters.

In preferred processes of the present invention, the composition which comprises a glycerol ester is from a natural source.

In alternative preferred processes of the present invention, the composition which comprises a glycerol ester is from a non-natural source.

In further alternative preferred processes of the present invention, the composition which comprises a glycerol ester is from a synthetic or a semi-synthetic source.

In preferred processes of the present invention, the composition which comprises a glycerol ester(s) is a natural oil.

Preferably, the natural oil is selected from almond oil, avocado oil, behen oil, brazil nut oil, cashew nut oil, castor oil, chia seed oil, cocoa butter oil, coconut oil, corn oil, cottonseed oil, linseed oil, grape seed, hemp seed, macadamia nut oil, mustard oil, olive oil, palm oil, palm kernel oil, peanut oil, pecan nut oil, perilla oil, poppyseed oil, pracaxi oil, rice bran oil, safflower oil, sea buckthorn oil, sesame oil, soybean oil, sunflower oil, vigna mungo oil, and walnut oil. More preferably, the natural oil is selected from linseed oil, olive oil, palm oil, palm kernel oil, rapeseed oil, and sunflower oil. Even more preferably, the natural oil is selected from olive oil, rapeseed oil, and sunflower oil.

In preferred processes of the present invention, the glycerol ester(s) present in the composition comprises at least one fatty acid residue, wherein the saturated or unsaturated aliphatic chain of the fatty acid residue comprises 12 to 24 carbon atoms, preferably 14 to 22 carbon atoms, more preferably 16 to 20 carbon atoms (e.g. 18 carbon atoms). The saturated or unsaturated aliphatic chain of the fatty acid residue may be unsubstituted or substituted.

Preferably, the glycerol ester(s) present in the composition comprises at least one fatty acid residue, wherein the saturated or unsaturated aliphatic chain of the fatty acid residue comprises 12 carbon atoms.

Preferably, the glycerol ester(s) present in the composition comprises at least one fatty acid residue, wherein the saturated or unsaturated aliphatic chain of the fatty acid residue comprises 14 carbon atoms.

Preferably, the glycerol ester(s) present in the composition comprises at least one fatty acid residue, wherein the saturated or unsaturated aliphatic chain of the fatty acid residue comprises 16 carbon atoms.

Preferably, the glycerol ester(s) present in the composition comprises at least one fatty acid residue, wherein the saturated or unsaturated aliphatic chain of the fatty acid residue comprises 18 carbon atoms.

Preferably, the glycerol ester(s) present in the composition comprises at least one fatty acid residue, wherein the saturated or unsaturated aliphatic chain of the fatty acid residue comprises 20 carbon atoms.

Preferably, the glycerol ester(s) present in the composition comprises at least one fatty acid residue, wherein the saturated or unsaturated aliphatic chain of the fatty acid residue comprises 22 carbon atoms.

Preferably, the glycerol ester(s) present in the composition comprises at least one fatty acid residue, wherein the saturated or unsaturated aliphatic chain of the fatty acid residue comprises 24 carbon atoms.

In preferred processes of the present invention, the glycerol ester(s) present in the composition comprises at least one fatty acid residue wherein the aliphatic chain of the fatty acid residue is unsaturated and comprises 1 to 5 carbon-carbon double bonds, preferably 1 to 4 carbon-carbon double bonds, more preferably 1 to 3 carbon-carbon double bonds, more preferably 1 to 2 carbon-carbon double bonds. The unsaturated aliphatic chain of the fatty acid residue may be unsubstituted or substituted. The unsaturated aliphatic chain of the fatty acid residue may contain cis- and/or trans-double bonds.

Preferably, the glycerol ester(s) present in the composition comprises at least one fatty acid residue wherein the aliphatic chain of the fatty acid residue is unsaturated and comprises 1 carbon-carbon double bond.

Preferably, the glycerol ester(s) present in the composition comprises at least one fatty acid residue wherein the aliphatic chain of the fatty acid residue is unsaturated and comprises 2 carbon-carbon double bonds.

In preferred processes of the present invention, the glycerol ester(s) present in the composition comprises at least one fatty acid residue selected from an omega-9 fatty acid, an omega-7 fatty acid, an omega-6 fatty acid, and an omega-3 fatty acid.

Suitable omega-9 fatty acids include hypogeic acid, oleic acid, elaidic acid, gondoic acid, mead acid, erucic acid, nervonic acid, and ximenic acid.

Suitable omega-7 fatty acids include 5-dodecenoic acid, 7-tetradecenoic acid, palmitoleic acid, vaccenic acid, rumenic acid, paullinic acid, 15-docosenoic acid, and 17-tetracosenoic acid.

Suitable omega-6 fatty acids include linoleic acid, gamma-linolenic acid, calendic acid, eicosadienoic acid, dihomo-gamma-linolenic acid, arachidonic acid, docosadienoic acid, adrenic acid, osbond acid, tetracosatetraenoic acid, and tetracosapentaenoic acid.

Suitable omega-3 fatty acids include hexadecatrienoic acid, α-linolenic acid, stearidonic acid, eicosatrienoic acid, eicosatetraenoic acid, eicosapentaenoic acid, heneicosapentaenoic acid, docosapentaenoic acid, clupanodonic acid, docosahexaenoic acid, tetracosapentaenoic acid, and tetracosahexaenoic acid.

In preferred processes of the present invention, the glycerol ester(s) present in the composition comprises at least one fatty acid residue selected from linoleic acid and oleic acid.

In preferred processes of the present invention, the glycerol ester(s) present in the composition comprises one fatty acid residue. In alternative preferred processes of the present invention, the glycerol ester(s) present in the composition comprises two fatty acid residues. In further alternative preferred processes of the present invention, the glycerol ester(s) present in the composition comprises three fatty acid residues. Preferred fatty acid residues are discussed above.

As will be understood by a skilled person, the products of the process of the present invention are a fatty alcohol(s) and glycerol. In preferred processes of the present invention, the process does not produce a hemiacetal by-product.

In the instance the glycerol ester present in the composition contains one or more alkenyl and/or alkynyl moieties, the process of the present invention preferably selectively hydrogenates the ester moiety over at least one of the unsaturated carbon-carbon bonds of the alkene(s) and/or alkyne(s). In some known processes, hydrogenation of such a substrate results in hydrogenation of the alkenyl and/or an alkynyl moiety only, meaning that a two-step procedure is required in order to result in hydrogenation of the ester moiety. An advantage of the present invention is therefore that the presence of an alkenyl and/or an alkynyl moiety is not detrimental to the reduction of the ester moiety; rather, the unsaturated C—C bond can be preserved under the conditions of the reaction, if desired.

Alternatively, in the instance the glycerol ester present in the composition contains one or more alkenyl and/or alkynyl moieties, the process of the present invention preferably hydrogenates both the ester moiety and the unsaturated carbon-carbon bond of the alkene(s) and/or alkyne(s).

In the instance the glycerol ester present in the composition contains a ketone and/or an aldehyde moiety, the process of the present invention preferably hydrogenates both the ester moiety and the carbon-oxygen double bond of the ketone and/or aldehyde.

In the instance the glycerol ester present in the composition contains one or more alkenyl and/or an alkynyl moieties, and a ketone and/or an aldehyde moiety, the process of the present invention preferably selectively hydrogenates both the ester moiety and the carbon-oxygen double bond of the ketone and/or aldehyde over at least one of the unsaturated carbon-carbon bonds of the alkene(s) and/or alkyne(s). Alternatively, in the instance the glycerol ester present in the composition contains one or more alkenyl and/or alkynyl moieties, and a ketone and/or an aldehyde moiety, the process of the present invention preferably hydrogenates the ester moiety, the unsaturated carbon-carbon bond of the alkene(s) and/or alkyne(s), and the carbon-oxygen double bond of the ketone and/or aldehyde.

In preferred processes of the present invention, the process is a batch process.

In preferred processes of the present invention, the process is a flow process. Preferably, the process is a flow process wherein any excess base is recycled.

The present invention also provides a hydrogenated composition obtained by or obtainable by the process as hereinbefore described.

The present invention also provides a method of making a compound, comprising a process as hereinbefore described.

The invention will now be further described by way of the following non-limiting examples.

EXAMPLES

Materials

Ru—SNS and Ru—PNN are commercially available from Johnson Matthey.

NaOEt is commercially available, e.g. from Sigma Aldrich, Fisher Scientific, Alfa Aesar, Acros Organics etc.

Rapeseed oil (RS1) is commercially available. The substrate composition of the rapeseed oil used in the following examples was found to be approximately: C16:0—5.6%, C18:0—1.3%, C18:1—61.6%, C18:2—21.4% by GC analysis.

Olive oil (OO1) is commercially available. The substrate composition of the olive oil used in the following examples was found to be approximately: C16:0—1.3%, C18:0—2.4%, C18:1—73.0%, C18:2—9.3% by GC analysis.

Sunflower oil (SO1) is commercially available. The substrate composition of the sunflower oil used in the following examples was found to be approximately: C16:0—6.1%, C18:0—2.5%, C18:1—23.3%, C18:2—66.1% by GC analysis.

Measurement Methods

Gas chromatography (GC) measurements were conducted using a Varian 3900 or 3800 gas chromatograph system.

Nuclear magnetic resonance (NMR) measurements were conducted using a Bruker Avance III 400 (400 MHz) spectrometer.

General Procedure for Hydrogenation of Glycerol Esters

To an 8 mL vial, catalyst Ru—SNS or Ru—PNN was added, followed by solid base, NaOEt, then solvent (if required), and then oil (RS1, OO1 or SO1). The vial was then added to a Biotage Endeavor screening system, before the stirring head was sealed and the reaction mixture purged with nitrogen. A purge sequence involved pressurizing to approximately 45 psi nitrogen and then releasing the pressure (repeated 5 times). The reactor was then pressurised with hydrogen then heated and pressurized to a set pressure of hydrogen. Once the reaction time was complete, typically 16 hrs, the reaction was allowed to cool to room temperature. Nitrogen purge cycles (5 repeats) were then carried out to remove hydrogen.

The reaction mixture was then analysed via GC and NMR. Before conducting the analysis, it was necessary to first add a small amount of EtOH to the crude reaction mixture and heat at 100° C. for 1 hour. The reaction mixture was then allowed to cool. For GC analysis, the reaction mixture was diluted with EtOH in a GC vial and GC analysis was performed. For NMR analysis, the reaction mixture was first subjected to a work-up procedure ((i) dilution with toluene and water plus addition of 4M HCl, (ii) separation of the aqueous layer, and (iii) removal of the organic solvent in vacuo), before NMR analysis was performed on the residue obtained.

Example 1: Investigation into Variation of Amount of Base

The General Procedure described above was carried out on a sample of rapeseed oil (RS1). The temperature, pressure, catalyst and catalyst loading were kept constant for each set of experiments, but the amount of solid base NaOEt used was varied. Toluene was additionally used as solvent when the Ru—SNS catalyst was employed. As Example 1 was a screening experiment, the crude reaction mixtures were not worked up, meaning that NMR conversions are not available. The reactions were instead monitored by GC analysis and hydrogen uptake. The results are shown in Table 1 below.

The results in Table 1 show that when the amount of base is increased, the C18:1 conversion for the hydrogenation reaction increases significantly despite the catalyst loading remaining very low. This was observed for both sets of experiments, i.e. those involving the Ru—PNN catalyst (entry 1 vs entry 2, and entry 3 vs entry 4) and those involving the Ru—SNS catalyst (entry 5 vs entry 6). In each set of experiments, the C18:1 conversion was found to increase as the amount of base was increased from 6.2 wt % to 18.7 wt %.

Example 2: Investigation into Delayed Start to Reaction

The General Procedure described above was carried out on a sample of rapeseed oil (RS1) using the Ru—SNS catalyst. The reactions were carried out using toluene as solvent, but varying amounts of EtOH were additionally employed to see if this had an effect on the reaction progress. As Example 2 was a screening experiment, the majority of the crude reaction mixtures were not worked up, meaning that NMR conversions are not available (aside from for entry 2, which was worked up and found to have an NMR conversion of 80%). The reactions were instead monitored by GC analysis and hydrogen uptake. The results are shown in Table 2 below.

As can be seen from Table 2, all of the reactions that were conducted at 50° C. were found to proceed with a full C18:1 conversion via GC except for entry 1, which did not contain any EtOH additive. As can be seen from FIG. 1, the delay to the reaction start time, as monitored by hydrogen uptake, was significantly reduced upon the addition of EtOH to the reaction mixture (i.e. ~16 h delay for entry 1 (no EtOH) versus ~2 h for entry 2, ~0.5 h for entry 3 and ~2.5 h for entry 4).

All of the reactions that were conducted at 60° C. were found to proceed with a full C18:1 conversion via GC. As can be seen from FIG. 2, the delay to the reaction start time, as monitored by hydrogen uptake, was again significantly reduced upon the addition of EtOH to the reaction mixture (i.e. ~13 h delay for entry 5 (no EtOH) versus ~3 h for entry 6, ~1 h for entry 7 and ~1 h for entry 8).

Figure 2:
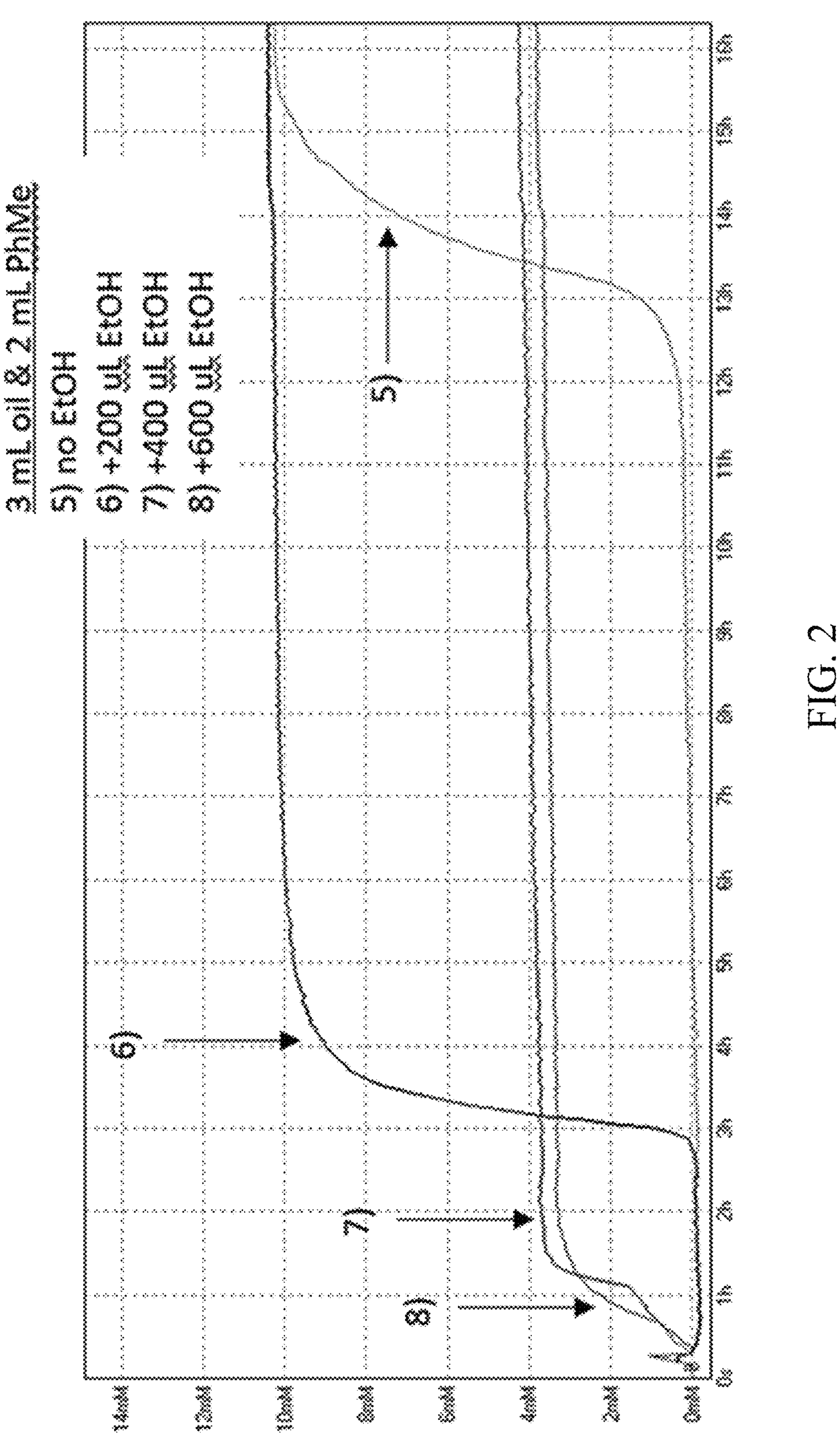
FIG. 2 is a hydrogen uptake curve (i.e. hydrogen uptake in mM (y axis) versus time (x axis)) for the experiments of entries 5-8 of Example 2.

The results shown in Table 2 and FIGS. 1 and 2 may also suggest that lower temperatures are more favourable.

Example 3: Glycerol Ester Hydrogenation

The General Procedure described above was carried out on a sample of rapeseed oil (RS1). The conditions used in each reaction are listed in Table 3 below. The results of each reaction are also listed in Table 3.

Example 4: Glycerol Ester Hydrogenation

The General Procedure described above was carried out on samples of rapeseed oil (RS1), olive oil (OO1) and sunflower oil (SO1). The conditions used in each reaction are listed in Table 4 below. The results of each reaction are also listed in Table 4.

The results in Tables 3 and 4 show that the process of the present invention can achieve high NMR conversion and mass recovery for the hydrogenation of a range of oils (i.e. compositions comprising glycerol esters) at extremely low catalyst loadings (e.g. about 0.0114 wt % based upon the amount of oil (which equates to approximately 19,000/1-20,000/1 S/C) for the experiments in Table 3 and about 0.0059 wt % based upon the amount of oil (which equates to approximately 38,000/1-40,000/1 S/C) for the experiments in Table 4). The results also show that a range of different transition metal catalysts containing tridentate ligands can be used to perform the hydrogenation reaction.

Comparison of entries 1 and 2 of Table 3 shows comparable results. Thus, when all other variables remain constant, the hydrogenation reaction conducted using Ru—SNS achieves a high NMR conversion and mass recovery even at a much lower pressure of 10 bar (compared to 30 bar in entry 2 of Table 3). The same can also be said for the hydrogenation reaction conducted using Ru—PNN (entries 3 and 4 of Table 3). Being able to operate the ester hydrogenation reaction of the present invention at lower pressures offers the additional advantages of reduced cost and improved safety. In addition, the need for specialist equipment that must withstand high pressures is avoided.

In some cases, the processes of the present invention are conducted in the absence of a solvent, whereas in other cases the present of a solvent has been found to be beneficial. The addition of a small amount of an alcohol (e.g. EtOH) has also been found to be beneficial in some instances (see Example 2 above). In the experiments shown in Tables 3 and 4, it was found that for RS1, the processes involving the Ru—SNS catalyst worked best in the presence of toluene as solvent, whereas the Ru—PNN catalyst worked best without solvent. OO1 and SO1 were able to better tolerate a range of solvent conditions, but the best conditions for both catalysts were found to be the use of toluene as solvent. All of the experiments in Tables 3 and 4 were, however, found to benefit from the addition of a small amount of EtOH, as this was found to help minimise the time delay to the hydrogenation reaction starting. The results shown in Tables 3 and 4 therefore demonstrate that the processes of the present invention can be effectively carried out using a range of different solvent conditions. As will be understood by a skilled person, optimised solvent conditions may vary from substrate to substrate.

Example 5: Parr Scale Glycerol Ester Hydrogenation

Rapeseed oil (RS1) (91 g, 100 mL), toluene (60 mL, 60 vol % based upon RS1) and then solid NaOEt (28.1 g, 30.9 wt % with respect to RS1 substrate) were added into a Parr 600 mL reaction vessel. The vessel and stirrer head were clamped together and assembled into the heating mantle. Nitrogen purges were completed on the vessel and stirring of the reaction mixture was set to approximately 750 rpm during this time. The mixture was heated to 40° C. and maintained at this level. Once the temperature of the system had equilibrated, the system was emptied of nitrogen and a slurry of EtOH (12 mL, 12 vol % based upon RS1) and Ru—SNS catalyst (10.4 mg, 0.0114 wt. % with respect to RS1 substrate) were added into the vessel via an injection port. 5 purges with hydrogen were completed and then the reaction pressure set to 30 bar and stirring turned to approximately 1500 rpm. The hydrogen pressure was maintained during the reaction and uptake was monitored. Following reaction overnight the reactor was allowed to cool, the hydrogen was carefully vented, and nitrogen purging performed to inert the reaction vessel.

The crude reaction mixture was worked upon using 4M HCl (105 mL) and an additional 100 mL toluene was added to support an organic phase. The organic phase was separated and concentrated in vacuo, to give 79 g of crude product (86.8% weight of original substrate mass). Analysis by NMR showed a 95% conversion of ester content to alcohols.

Example 6: Parr Scale Glycerol Ester Hydrogenation

The reaction of Example 5 was repeated using 20.2 g of NaOEt (22.2 wt % with respect to RS1 substrate). Following work-up as described above for Example 5, 85 g of crude product was obtained (93.4% weight of original substrate mass). Analysis by NMR showed a 96% conversion of ester content to alcohols.

TABLE 1

[Amounts used: oil - 3 mL (2.73 g), catalyst - 0.00125 g (Ru-SNS, 0.0458 wt. %) or 0.00150 g (Ru-PNN, 0.0549 wt. %) or 0.00075 g (Ru-PNN, 0.0275 wt. %), base - 0.17 g (6.2 wt %) or 0.51 g (18.7 wt %)].

| Entry | Substrate | Catalyst | Catalyst (wt. %) | Loading (~S/C)[1] | Base (wt. %)[2] | Temperature (° C.) | Pressure (bar) | GC (%) C16:0 | GC (%) C18:0 | GC (%) C18:1 | GC (%) C18:2 | GC (%) Ethyl Oleate | C18:1 conv. (%) | Solvent |
|---|---|---|---|---|---|---|---|---|---|---|---|---|---|---|
| 1 | RS1 | Ru-PNN | 0.0549 | ~5000 | 6.2 | 80 | 30 | 0.7 | 0.3 | 17.5 | 3.6 | 39.8 | 30.5 | — |
| 2 | RS1 | Ru-PNN | 0.0549 | ~5000 | 18.7 | 80 | 30 | 5.3 | 3.4 | 61.8 | 12.1 | 0.0 | 100.0 | — |
| 3 | RS1 | Ru-PNN | 0.0275 | ~10000 | 6.2 | 80 | 30 | 1.5 | 0 | 23.6 | 6.9 | 33.6 | 41.3 | — |
| 4 | RS1 | Ru-PNN | 0.0275 | ~10000 | 18.7 | 80 | 30 | 3.7 | 0.4 | 49.5 | 15.5 | 11.7 | 80.9 | — |
| 5 | RS1 | Ru-SNS | 0.0458 | ~5000 | 6.2 | 80 | 30 | 0.9 | 0 | 18.1 | 4.4 | 39.6 | 31.4 | 2 mL PhMe |
| 6 | RS1 | Ru-SNS | 0.0458 | ~5000 | 18.7 | 80 | 30 | 5.1 | 4.3 | 64.1 | 14.2 | 0.0 | 100.0 | 2 mL PhMe |

[1] An approximation of S/C ratio can be made by assuming that the RS1 oil composition is entirely triglyceride with 100% C18:1 (i.e. mw = 846).

[2] The amount of base can be converted to an approximate mol % value with respect to ester content by assuming that the oil composition is entirely triglyceride with 100% C18:1 (i.e. mw = 846). Taking entry 2 as an example, the amount of base used equates to approximately 77 mol % with respect to ester content.

TABLE 2

[Amounts used: oil - 3 mL (2.73 g), catalyst - 0.00125 g (Ru-SNS), base - 0.85 g].

| Entry | Substrate | Catalyst | Catalyst (wt. %) | Loading (~S/C)[1] | Base (wt. %)[2] | Temperature (° C.) | Pressure (bar) | GC (%) C16:0 | GC (%) C18:0 | GC (%) C18:1 | GC (%) C18:2 | GC (%) Ethyl Oleate | C18:1 conv. (%) | Solvent |
|---|---|---|---|---|---|---|---|---|---|---|---|---|---|---|
| 1 | RS1 | Ru-SNS | 0.0458 | ~5000 | 31.1 | 50 | 30 | 1.7 | 0 | 27.7 | 5.7 | 41.1 | 40.3 | 2 mL PhMe |
| 2 | RS1 | Ru-SNS | 0.0458 | ~5000 | 31.1 | 50 | 30 | 4 | 0.5 | 69.2 | 13.8 | 0.0 | 100.0 | 2 mL PhMe 0.2 mL EtOH |
| 3 | RS1 | Ru-SNS | 0.0458 | ~5000 | 31.1 | 50 | 30 | 5.4 | 1 | 65.3 | 16.6 | 0.0 | 100.0 | 2 mL PhMe 0.4 mL EtOH |
| 4 | RS1 | Ru-SNS | 0.0458 | ~5000 | 31.1 | 50 | 30 | 5.1 | 1 | 65.8 | 17.2 | 0.0 | 100.0 | 2 mL PhMe 0.66 mL EtOH |
| 5 | RS1 | Ru-SNS | 0.0458 | ~5000 | 31.1 | 60 | 30 | 5.3 | 1 | 63.3 | 17.1 | 0.0 | 100.0 | 2 mL PhMe |
| 6 | RS1 | Ru-SNS | 0.0458 | ~5000 | 31.1 | 60 | 30 | 6.1 | 1.1 | 63.9 | 16.5 | 0.0 | 100.0 | 2 mL PhMe 0.2 mL EtOH |
| 7 | RS1 | Ru-SNS | 0.0458 | ~5000 | 31.1 | 60 | 30 | 4.8 | 1.3 | 63.5 | 17.9 | 0.0 | 100.0 | 2 mL PhMe 0.4 mL EtOH |
| 8 | RS1 | Ru-SNS | 0.0458 | ~5000 | 31.1 | 60 | 30 | 5.5 | 1.1 | 65.4 | 14.9 | 0.0 | 100.0 | 2 mL PhMe 0.6 mL EtOH |

[1]An approximation of S/C ratio can be made by assuming that the RS1 oil composition is entirely triglyceride with 100% C18:1 (i.e. mw = 846).

[2]The amount of base can be converted to an approximate mol % value with respect to ester content by assuming that the oil composition is entirely triglyceride with 100% C18:1 (i.e. mw = 846). Taking entry 1 as an example, the amount of base used equates to approximately 129 mol % with respect to ester content.

TABLE 3

[Amounts used: oil - 3 mL (2.73 g), catalyst - 0.0003125 g (Ru-SNS) or 0.000375 g (Ru-PNN), base - 0.85 g].

| Entry | Substrate | Catalyst | Catalyst (wt. %) | Loading (~S/C)[1] | Base (wt. %)[2] | Temperature (° C.) | Pressure (bar) | Uptake ($H_2$) | NMR Conversion | Mass Recovered (% of substrate mass) | Solvent |
|---|---|---|---|---|---|---|---|---|---|---|---|
| 1 | RS1 | Ru-SNS | 0.0114 | 19000-20000 | 31.1 | 40 | 30 | 15.4 | 89% | 2 g (73%) | 2 mL PhMe 0.4 mL EtOH |
| 2 | RS1 | Ru-SNS | 0.0114 | 19000-20000 | 31.1 | 40 | 10 | 14.4 | 87% | 2 g (73%) | 2 mL PhMe 0.4 mL EtOH |
| 3 | RS1 | Ru-PNN | 0.0137 | 19000-20000 | 31.1 | 40 | 30 | 14.4 | 89% | 1.3 g (48%) | 0 mL PhMe 0.4 mL EtOH |
| 4 | RS1 | Ru-PNN | 0.0137 | 19000-20000 | 31.1 | 40 | 10 | 15.0 | 89% | 1.2 g (44%) | 0 mL PhMe 0.4 mL EtOH |

[1]An approximation of S/C ratio can be made by assuming that the RS1 oil composition is entirely triglyceride with 100% C18:1 (i.e. mw = 846).

[2]The amount of base can be converted to an approximate mol % value with respect to ester content by assuming that the RS1 oil composition is entirely triglyceride with 100% C18:1 (i.e. mw = 846). Taking entry 1 as an example, the amount of base used equates to approximately 129 mol % with respect to ester content.

For the results in Table 3, the worked-up chain distributions (%) were as follows (order = C16:0, C18:0, C18:1, C18:2, Ethyl Oleate):

Entry 1: 4.3, 0, 62.8, 20.4, 0

Entry 2: 4.2, 0, 63.0, 20.5, 0

Entry 3: 4.3, 1.0, 63.1, 20.4, 0

Entry 4: 4.3, 1.0, 63.3, 20.6, 0

TABLE 4

[Amounts used: oil - 3 mL (2.73 g), catalyst 0.00015625 g (Ru-SNS) or 0.0001875 g (Ru-PNN), base - 0.85 g].

| Entry | Substrate | Catalyst | Catalyst (wt. %) | Loading (~S/C)[1] | Base (wt. %)[2] | Temperature (° C.) | Pressure (bar) | Uptake ($H_2$) | NMR Conversion | Mass Recovered (% of substrate mass | Solvent |
|---|---|---|---|---|---|---|---|---|---|---|---|
| 1 | RS1 | Ru-SNS | 0.0059 | 38000-40000 | 31.1 | 40 | 30 | 15.2 | 84% | 1.9 g (70%) | 2 mL PhMe 0.4 mL EtOH |
| 2 | OO1 | Ru-SNS | 0.0059 | 38000-40000 | 31.1 | 40 | 30 | 15.3 | 88% | 2.2 g (81%) | 2 mL PhMe 0.4 mL EtOH |
| 3 | OO1 | Ru-PNN | 0.0069 | 38000-40000 | 31.1 | 40 | 30 | 13.7 | 87% | 2.3 g (84%) | 2 mL PhMe 0.4 mL EtOH |
| 4 | SO1 | Ru-SNS | 0.0059 | 38000-40000 | 31.1 | 40 | 10 | 12.2 | 70% | 2.35 g (86%) | 2 mL PhMe 0.4 mL EtOH |
| 5 | SO1 | Ru-PNN | 0.0069 | 38000-40000 | 31.1 | 40 | 30 | 14.6 | 78% | 2.3 g (84%) | 2 mL PhMe 0.4 mL EtOH |

[1]An approximation of S/C ratio can be made by assuming that the oil composition is entirely triglyceride with 100% C18:1 (i.e. mw = 846).

[2]The amount of base can be converted to an approximate mol % value with respect to ester content by assuming that the oil composition is entirely triglyceride with 100% C18:1 (i.e. mw = 846). Taking entry 1 as an example, the amount of base used equates to approximately 129 mol % with respect to ester content.

For the results in Table 4, the worked-up chain distributions (in %) were as follows (order = C16:0, C18:0, C18:1, C18:2, ethyl oleate):

Entry 1: 4.3, 0, 60.8, 19.5, 0

Entry 2: 11.2, 2.8, 73.7, 8.3, 0

Entry 3: 11.2, 2.7, 74.2, 8.3, 0

Entry 4: 6.1, 3.6, 26.4, 61.2, 0

Entry 5: 6.3, 3.4, 26.6, 62.0, 0

The invention claimed is:

1. A process for hydrogenation of a glycerol ester, comprising treating a composition which comprises the glycerol ester with a base and a transition metal catalyst in the presence of molecular hydrogen, wherein the base is present in at least 7 wt % based upon the total weight of said composition and wherein the catalyst is present in less than or equal to 0.05 wt % based upon the total weight of said composition, wherein the transition metal catalyst comprises a transition metal that is Ru or Os and a tridentate ligand having a structure of Formula (I):

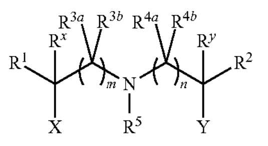

(I)

wherein:

X is —$SR^a$, —$OR^a$, —$CR^a$, —$NR^aR^b$, —$PR^aR^b$, —$P(═O)R^aR^b$, —$OPR^aR^b$, or —$NHPR^aR^b$;

$R^1$ and $R^x$ are each, independently, hydrogen, substituted $C_{1-20}$-alkyl, unsubstituted $C_{1-20}$-alkyl, substituted $C_{2-20}$-alkenyl, unsubstituted $C_{2-20}$-alkenyl, substituted $C_{2-20}$-alkynyl, unsubstituted $C_{2-20}$-alkynyl, substituted $C_{1-20}$-heteroalkyl, unsubstituted $C_{1-20}$-heteroalkyl, substituted $C_{1-20}$-alkoxy, unsubstituted $C_{1-20}$-alkoxy, substituted $C_{3-20}$-cycloalkyl, unsubstituted $C_{3-20}$-cycloalkyl, substituted $C_{3-20}$-cycloalkenyl, unsubstituted $C_{3-20}$-cycloalkenyl, substituted $C_{2-20}$-heterocycloalkyl, unsubstituted $C_{2-20}$-heterocycloalkyl, substituted $C_{6-20}$-aryl, unsubstituted $C_{6-20}$-aryl, substituted $C_{4-20}$-heteroaryl, or unsubstituted $C_{4-20}$-heteroaryl;

or $R^1$ and one of $R^{3a}$ and $R^{3b}$ or $R^x$ and one of $R^{3a}$ and $R^{3b}$ together with the atoms to which they are bound, form a ring;

or X is a heteroatom and when taken together with $R^1$ it forms an optionally substituted heterocycle when $R^x$ is absent;

Y is —$SR^a$, —$OR^a$, —$CR^a$, —$NR^aR^b$, —$PR^aR^b$, —$P(═O)R^aR^b$, —$OPR^aR^b$, or —$NHPR^aR^b$;

$R^2$ and $R^y$ are each, independently, hydrogen, substituted $C_{1-20}$-alkyl, unsubstituted $C_{1-20}$-alkyl, substituted $C_{2-20}$-alkenyl, unsubstituted $C_{2-20}$-alkenyl, substituted $C_{2-20}$-alkynyl, unsubstituted $C_{2-20}$-alkynyl, substituted $C_{1-20}$-heteroalkyl, unsubstituted $C_{1-20}$-heteroalkyl, substituted $C_{1-20}$-alkoxy, unsubstituted $C_{1-20}$-alkoxy, substituted $C_{3-20}$-cycloalkyl, unsubstituted $C_{3-20}$-cycloalkyl, substituted $C_{3-20}$-cycloalkenyl, unsubstituted $C_{3-20}$-cycloalkenyl, substituted $C_{2-20}$-heterocycloalkyl, unsubstituted $C_{2-20}$-heterocycloalkyl, substituted $C_{6-20}$-aryl, unsubstituted $C_{6-20}$-aryl, $C_{4-20}$-heteroaryl substituted, or unsubstituted $C_{4-20}$-heteroaryl;

or $R^2$ and one of $R^{4a}$ and $R^{4b}$ or $R^y$ and one of $R^{4a}$ and $R^{4b}$ together with the atoms to which they are bound, form a ring;

or Y is a heteroatom and when taken together with $R^2$ it forms an optionally substituted heterocycle when $R^y$ is absent;

$R^{3a}$, $R^{3b}$, $R^{4a}$ and $R^{4b}$ are each, independently, hydrogen, substituted $C_{1-20}$-alkyl, unsubstituted $C_{1-20}$-alkyl, substituted $C_{2-20}$-alkenyl, unsubstituted $C_{2-20}$-alkenyl, substituted $C_{2-20}$-alkynyl, unsubstituted $C_{2-20}$-alkynyl, substituted $C_{1-20}$-heteroalkyl, unsubstituted $C_{1-20}$-heteroalkyl, substituted $C_{1-20}$-alkoxy, unsubstituted $C_{1-20}$-alkoxy, substituted $C_{3-20}$-cycloalkyl, unsubstituted $C_{3-20}$-cycloalkyl, substituted $C_{3-20}$-cycloalkenyl, unsubstituted $C_{3-20}$-cycloalkenyl, substituted $C_{3-20}$-cycloalkenyl, unsubstituted $C_{2-20}$-heterocycloalkyl, substituted $C_{6-20}$-aryl, unsubstituted $C_{6-20}$-aryl, substituted $C_{4-20}$-heteroaryl, or unsubstituted $C_{4-20}$-heteroaryl;

or $R^{3a}$ and one of $R^{4a}$ and $R^{4b}$ or $R^{3b}$ and one of $R^{4a}$ and $R^{4b}$, together with the atoms to which they are bound, form a heterocycle;

$R^5$ is hydrogen, substituted $C_{1-20}$-alkyl, unsubstituted $C_{1-20}$-alkyl, substituted $C_{2-20}$-alkenyl, unsubstituted $C_{2-20}$-alkenyl, substituted $C_{2-20}$-alkynyl, unsubstituted $C_{2-20}$-alkynyl, substituted $C_{1-20}$-heteroalkyl, unsubstituted $C_{1-20}$-heteroalkyl, substituted $C_{1-20}$-alkoxy, unsubstituted $C_{1-20}$-alkoxy, substituted $C_{3-20}$-cycloalkyl, unsubstituted $C_{3-20}$-cycloalkyl, substituted $C_{3-20}$-cycloalkenyl, unsubstituted $C_{3-20}$-cycloalkenyl, substituted $C_{2-20}$-heterocycloalkyl, unsubstituted $C_{2-20}$-heterocycloalkyl, substituted $C_{6-20}$-aryl, unsubstituted $C_{6-20}$-aryl, substituted $C_{4-20}$-heteroaryl, or unsubstituted $C_{4-20}$-heteroaryl;

each m and n is, independently, 1 or 2; and $R^a$ and $R^b$, if present, are each, independently, hydrogen, substituted $C_{1-20}$-alkyl, unsubstituted $C_{1-20}$-alkyl, substituted $C_{2-20}$-alkenyl, unsubstituted $C_{2-20}$-alkenyl, substituted $C_{2-20}$-alkynyl, unsubstituted $C_{2-20}$-alkynyl, substituted $C_{1-20}$-heteroalkyl, unsubstituted $C_{1-20}$-heteroalkyl, substituted $C_{1-20}$-alkoxy, unsubstituted $C_{1-20}$-alkoxy, substituted $C_{3-20}$-cycloalkyl, unsubstituted $C_{3-20}$-cycloalkyl, substituted $C_{3-20}$-cycloalkenyl, unsubstituted $C_{3-20}$-cycloalkenyl, substituted $C_{2-20}$-heterocycloalkyl, unsubstituted $C_{2-20}$-heterocycloalkyl, substituted $C_{6-20}$-aryl, unsubstituted $C_{6-20}$-aryl, substituted $C_{4-20}$-heteroaryl, or unsubstituted $C_{4-20}$-heteroaryl;

or when X and/or Y is —$NR^aR^b$, —$PR^aR^b$, —$OPR^aR^b$, or —$NHPR^aR^b$, $R^a$ and $R^b$ together with the heteroatom to which they are attached form a heterocycle.

2. The process of claim 1, wherein the base is present in at least 7.5 wt % based upon the total weight of said composition which comprises the glycerol ester.

3. The process of claim 1, wherein the base is a metal alkoxide.

4. The process of claim 1, wherein the base is an alkali metal ethoxide that is lithium ethoxide, sodium ethoxide or potassium ethoxide.

5. The process of claim 1, wherein the process is carried out in the absence of solvent.

6. The process of claim 1, wherein the process is carried out in the presence of at least one solvent that is an alcohol, toluene, THF, or Me-THF.

7. The process of claim 6, wherein said at least one solvent is present in an amount of 10 to 100 vol % based upon the total volume of said composition which comprises the glycerol ester.

8. The process of claim 6, wherein the at least one solvent is an alcohol, toluene, THF, or Me-THF.

9. The process of claim 1, wherein the process is carried out in the presence of a first solvent and a second solvent.

10. The process of claim 9, wherein said first solvent is toluene or THE and said second solvent is an alcohol.

11. The process of claim 9, wherein said first solvent is present in an amount of 10 to 100 vol % based upon the total volume of said composition which comprises the glycerol ester.

12. The process of claim 9, wherein said second solvent is present in an amount of 1 to 15 vol % based upon the total volume of said composition which comprises the glycerol ester.

13. The process of claim 1, wherein the process is performed at a temperature in the range 20 to 150° C.

14. The process of claim 1, wherein the process is performed at a pressure in the range 5 to 100 bar.

15. The process of claim 1, wherein the catalyst is present in less than or equal to 0.04 wt % based upon the total weight of the composition which comprises the glycerol ester.

16. The process of claim 1, wherein the catalyst is present in less than or equal to 0.005 wt% based upon the total weight of the composition which comprises the glycerol ester.

17. The process of claim 1, wherein the transition metal catalyst has a Formula (II) or Formula (III)

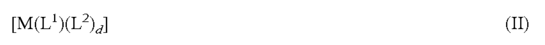

$$[M(L^1)(L^2)_d] \quad (II)$$

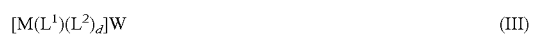

$$[M(L^1)(L^2)_d]W \quad (III)$$

wherein:

M is Ru or Os;

$L^1$ is the tridentate ligand Formula (I);

$L^2$ are ligands which are the same or different;

d is 1, 2 or 3; and

W is a non-coordinated anionic ligand.

18. The process of claim 17, wherein each $L^2$ is, independently, —H, —CO, —CN, —$P(R')_3$, —$As(R')_3$, —CR', —OR', —O(C═O)R', —$NR'_2$, halogen, or a solvent wherein each R' is, independently, substituted alkyl, unsubstituted alkyl, substituted alkenyl, unsubstituted alkenyl, substituted alkynyl, unsubstituted alkynyl, substituted heteroalkyl, unsubstituted heteroalkyl, substituted alkoxy, unsubstituted alkoxy, substituted cycloalkyl, unsubstituted cycloalkyl, substituted heterocycloalkyl, unsubstituted heterocycloalkyl, substituted aryl, unsubstituted aryl, substituted heteroaryl, or unsubstituted heteroaryl.

19. The process of claim 1, wherein the transition metal catalyst is

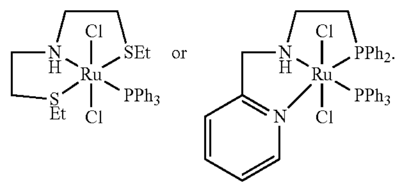

20. The process of claim 1, wherein the composition which comprises the glycerol ester is a natural oil that is almond oil, avocado oil, behen oil, brazil nut oil, cashew nut oil, castor oil, chia seed oil, cocoa butter oil, coconut oil, corn oil, cottonseed oil, linseed oil, grape seed, hemp seed, macadamia nut oil, mustard oil, olive oil, palm oil, palm kernel oil, peanut oil, pecan nut oil, perilla oil, poppyseed oil, pracaxi oil, rice bran oil, safflower oil, sea buckthorn oil, sesame oil, soybean oil, sunflower oil, vigna mungo oil, or walnut oil.

21. The process of claim 1, wherein the base is present in at least 8 wt % based upon the total weight of said composition which comprises the glycerol ester.

22. The process of claim 1, wherein the base is present in at least 8.5 wt % based upon the total weight of said composition which comprises the glycerol ester.

23. The process of claim 1, wherein the base is present in at least 9 wt % based upon the total weight of said composition which comprises the glycerol ester.

24. The process of claim 1, wherein the base is an alkali metal alkoxide.

* * * * *